(12) United States Patent
Milstein et al.

(10) Patent No.: US 7,005,141 B2
(45) Date of Patent: *Feb. 28, 2006

(54) ORAL DRUG DELIVERY COMPOSITIONS AND METHODS

(75) Inventors: Sam J. Milstein, Larchmont, NY (US); Evgueni N. Barantsevitch, New Rochelle, NY (US); Donald J. Sarubbi, Bronxville, NY (US); Andrea Leone-Bay, Ridgefield, CT (US); Duncan R. Paton, Purdys, NY (US)

(73) Assignee: Emisphere Technologies Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/225,104

(22) Filed: Aug. 20, 2002

(65) Prior Publication Data

US 2003/0012817 A1  Jan. 16, 2003

Related U.S. Application Data

(63) Continuation of application No. 09/862,063, filed on May 21, 2001, now Pat. No. 6,461,643, which is a continuation of application No. 09/346,971, filed on Jul. 2, 1999, now abandoned, which is a continuation of application No. 08/438,644, filed on May 10, 1995, now Pat. No. 5,958,457, which is a continuation-in-part of application No. 08/335,147, filed on Oct. 25, 1994, now abandoned, and a continuation-in-part of application No. PCT/US94/04560, filed on Apr. 22, 1994, and a continuation-in-part of application No. 08/231,622, filed on Apr. 22, 1994, now Pat. No. 5,629,020, and a continuation-in-part of application No. 08/205,511, filed on Mar. 2, 1994, now Pat. No. 5,792,451, which is a continuation-in-part of application No. 08/051,019, filed on Apr. 22, 1993, now Pat. No. 5,451,410.

(51) Int. Cl.
*A61K 9/20* (2006.01)

(52) U.S. Cl. ............... 424/464; 424/451; 424/489; 424/491; 424/499; 514/533; 514/561

(58) Field of Classification Search ............... 424/489, 424/451, 464, 491, 499; 514/553, 561
See application file for complete search history.

(56) References Cited

U.S. PATENT DOCUMENTS

4,610,983 A   9/1986  Takagawa et al.

(Continued)

FOREIGN PATENT DOCUMENTS

| FR | 4446 | 11/1966 |
| JP | 48-37819 | 11/1973 |
| WO | WO-96/30036 | 10/1996 |

(Continued)

OTHER PUBLICATIONS

Palagiano, F. et al.: "Synthesis, stability and anticonvulsant activity of two new GABA prodrugs," *Pharamazic*, 52 (4): 272-276 (1997), XP-001084051.

(Continued)

*Primary Examiner*—Thurman K. Page
*Assistant Examiner*—Lakshmi Channavajjala
(74) *Attorney, Agent, or Firm*—Darby & Darby

(57) ABSTRACT

The present invention relates to an oral drug delivery system, and in particular to modified amino acids and modified amino acid derivatives for use as a delivery system of sensitive agents such as bioactive peptides. The modified amino acids and derivatives can form non-covalent mixtures with active biological agents and in an alternate embodiment can releasably carry active agents. Modified amino acids can also form drug containing microspheres. These mixtures are suitable for oral administration of biologically active agents to animals. Methods for the preparation of such amino acids are also disclosed.

46 Claims, 22 Drawing Sheets

U.S. PATENT DOCUMENTS

| | | | |
|---|---|---|---|
| 5,650,386 A | | 7/1997 | Leone-Bay et al. |
| 5,705,529 A | | 1/1998 | Matyus et al. |
| 5,766,633 A | * | 6/1998 | Milstein et al. ............. 424/489 |
| 5,773,647 A | * | 6/1998 | Leone-Bay et al. ......... 562/444 |
| 5,776,888 A | | 7/1998 | Leone-Bay et al. |
| 5,792,451 A | * | 8/1998 | Sarubbi et al. ............. 424/85.4 |
| 5,804,688 A | * | 9/1998 | Leone-Bay et al. ......... 562/444 |
| 5,876,710 A | * | 3/1999 | Leone-Bay et al. ........ 424/85.1 |
| 6,060,513 A | * | 5/2000 | Leone-Bay et al. ......... 514/559 |
| 6,344,213 B1 | | 2/2002 | Leone-Bay et al. |
| 6,461,643 B1 | * | 10/2002 | Milstein et al. ............. 424/489 |

FOREIGN PATENT DOCUMENTS

| | | |
|---|---|---|
| WO | WO-98/21951 | 5/1998 |
| WO | WO 99/29705 | 6/1999 |

OTHER PUBLICATIONS

Yalcin, I. et al.: "Synthesis and Microbiological Activity of Some Novel N-(2-Hydroxyl-5-Substitutedphenyl)Benzacetamides, Phenoxyacetamides and Thiophenoxycetamides as the Possible Metabolites of Antimicrobial Active Benzoxazoles," *Il Farmaco*, 52 (11), 685-689 (1997).

* cited by examiner 4-(Phenylsulfonamido)-4-phenylbutyric acid (800 mg/kg in Tris-HCl) and Interferon a2b (1000ug/kg)

ORAL DRUG DELIVERY COMPOSITIONS AND METHODS

This application is a continuation of U.S. application Ser. No. 09/862,063, filed now May 21, 2001; now U.S. Pat. No. 6,461,643, which is a continuation of U.S. application Ser. No. 09/346,971, filed Jul. 2, 1999, now abandoned; which is a continuation of U.S. application Ser. No. 08/438,644, filed May 10, 1995, now U.S. Pat. No. 5,958,457; which is a continuation-in-part of (a) U.S. application Ser. No. 08/335,147, filed Oct. 25, 1994, now abandoned; (b) PCT Application Serial No. PCT/US94/04560 filed Apr. 22, 1994; which is a continuation-in-part of U.S. application Ser. No. 08/051,019, filed Apr. 22, 1993, now U.S. Pat. No. 5,451,410; and of U.S. application Ser. No. 08/205,511, filed Mar. 2, 1994, now U.S. Pat. No. 5,792,451; and (c) U.S. application Ser. No. 08/231,622, filed Apr. 22, 1994, now U.S. Pat. No. 5,629,020. These prior applications are hereby incorporated herein by reference, in their entirety.

FIELD OF THE INVENTION

The present invention relates to compositions suitable for oral drug delivery, and in particular to compositions in which modified amino acids and modified amino acid derivatives are used as carriers for sensitive agents such as bioactive peptides and the like. The modified amino acids or derivatives can form non-covalent mixtures with biologically-active agents which are suitable for oral administration to animals. Methods for the preparation and for the administration of such compositions are also disclosed.

BACKGROUND OF THE INVENTION

Conventional means for delivering biologically-active agents, including, but not limited to, pharmaceutical and therapeutic agents, to animals are often severely limited by chemical barriers and physical barriers imposed by the body. Oral delivery of many biologically-active agents would be the route of choice if not for chemical and physico-chemical barriers such as the extreme and varying pH in the gastro-intestinal (GI) tract, exposure to powerful digestive enzymes, and the impermeability of gastro-intestinal membranes to the active agent. Among the numerous agents which are not typically suitable for oral administration are biologically active peptides such as calcitonin and insulin. Examples of other compounds which are affected by these physico-chemical barriers are polysaccharides and particularly mucopolysaccharides, including, but not limited to, heparin; heparinoids; antibiotics; and other organic substances. These agents are rapidly destroyed in the gastro-intestinal tract by acid hydrolysis, enzymes, or the like.

Prior methods for orally administering vulnerable pharmacological agents have relied on the co-administration of adjuvants (e.g., resorcinols and non-ionic surfactants such as polyoxyethylene oleyl ether and n-hexadecyl polyethylene ether) to increase artificially the permeability of the intestinal walls; and on the co-administration of enzymatic inhibitors (e.g., pancreatic trypsin inhibitor, diisopropylfluorophosphate (DFF) and trasylol) to inhibit enzymatic degradation. Liposomes have also been described as drug delivery systems for insulin and heparin. See, for instance, U.S. Pat. No. 4,239,754; Patel et al. (1976) *FEBS Letters* Vol. 62, page 60; and Hashimoto et al. (1979) *Endocrinol. Japan*, Vol. 26, page 337. However, broad spectrum use of the aforementioned drug delivery systems is precluded for reasons including: (1) the need to use toxic amounts of adjuvants or inhibitors; (2) the lack of suitable low MW cargoes; (3) the poor stability and inadequate shelf life of the systems; (4) the difficulties in manufacturing the systems; (5) the failure of the systems to protect the active ingredient; and (6) the failure of the systems to promote absorption of the active agent.

More recently, microspheres of artificial polymers or proteinoids of mixed amino acids have been described for delivery of pharmaceuticals. For example, U.S. Pat. No. 4,925,673 describes drug containing microsphere constructs as well as methods for their preparation and use. These proteinoid microspheres are useful for delivery of a number of active agents.

There is still a need in the art for simple and inexpensive delivery systems which are easily prepared and which can deliver a broad range of biologically-active agents.

SUMMARY OF THE INVENTION

Compositions for orally delivering biologically-active agents incorporating modified amino acids, amino acid derivatives, peptides and peptide derivatives as carriers are provided. These compositions comprise
(A) at least one biologically-active agent; and
(B) at least one carrier comprising
  (a) (i) at least one acylated aldehyde of an amino acid,
   (ii) at least one acylated ketone of an amino acid,
   (iii) at least one acylated aldehyde of a peptide,
   (iv) at least one acylated ketone of a peptide, or
   (v) any combination of (a)(i), (a)(ii), (a)(iii) and (a)(iv);
  (b) (i) carboxymethyl-phenylalanine-leucine,
   (ii) 2-carboxy-3-phenylpropionyl-leucine,
   (iii) 2-benzylsuccinic acid,
   (iv) an actinonin, or
   (v) a compound having the formula:

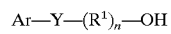

wherein: Ar is a substituted or unsubstituted phenyl or naphthyl;
Y is

or $-SO_2-$;
$R^1$ is

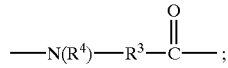

wherein:
$R^3$ is $C_1$ to $C_{24}$ alkyl, $C_1$ to $C_{24}$ alkenyl, phenyl, naphthyl, ($C_1$ to $C_{10}$ alkyl)phenyl, ($C_1$ to $C_{10}$ alkenyl)phenyl, ($C_1$ to $C_{10}$ alkyl) naphthyl, ($C_1$ to $C_{10}$ alkenyl) naphthyl, phenyl($C_1$ to $C_{10}$ alkyl), phenyl($C_1$ to $C_{10}$ alkenyl), naphthyl($C_1$ to $C_{10}$ alkyl) and naphthyl($C_1$ to $C_{10}$ alkenyl);
$R^3$ is optionally substituted with $C_1$ to $C_4$ alkyl, $C_1$ to $C_4$ alkenyl, $C_1$ to $C_4$ alkoxy, $-OH$, $-SH$, $-CO_2R^5$, cycloalkyl, cycloalkenyl, heterocyclic, aryl, alkaryl, heteroaryl or heteroalkaryl or any combination thereof;

$R^5$ is hydrogen, $C_1$ to $C_4$ alkyl or $C_1$ to $C_4$ alkenyl;
$R^3$ is optionally interrupted by oxygen, nitrogen, sulfur or any combination thereof; and
$R^4$ is hydrogen, $C_1$ to $C_4$ alkyl or $C_1$ to $C_4$ alkenyl; and n is from 1 to about 5;
(vi) or any combination of (b)(i), (b)(ii), (b)(iii), (b)(iv) and (b)(v); or
(c) a combination of (a) and (b).

Also contemplated is a method for preparing these compositions which comprises mixing at least one biologically active agent, with at least one carrier as described above, and optionally, a dosage vehicle.

In an alternative embodiment, these non-toxic carriers are orally administered to animals as part of a delivery system by blending or mixing the carriers with a biologically active agent prior to administration. The carriers may also form microspheres in the presence of the active agent. The microspheres containing the active agent are then orally administered. Also contemplated by the present invention are dosage unit forms that include these compositions.

DETAILED DESCRIPTION OF THE INVENTION

Figure 1:
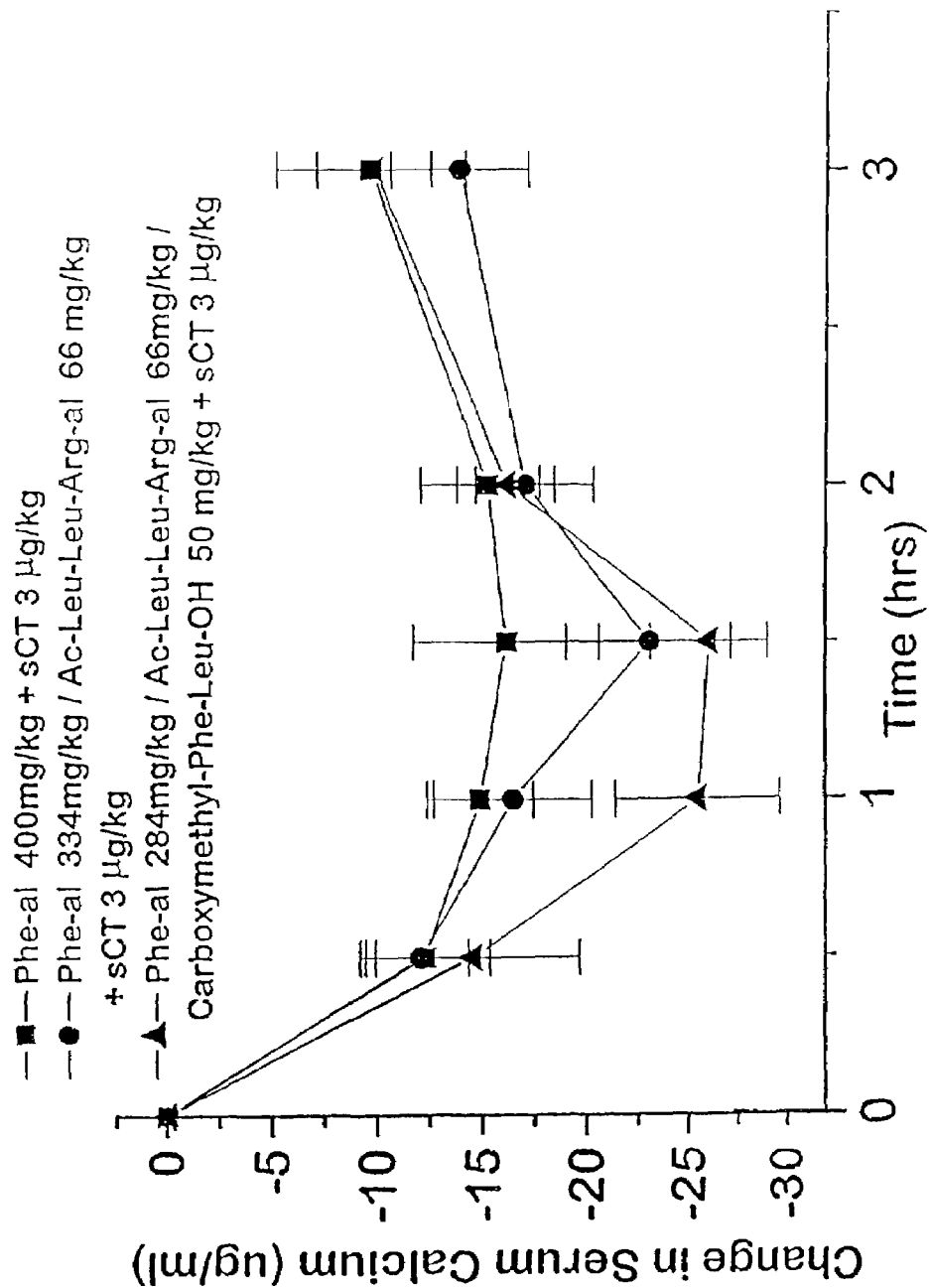
FIG. 1 is a graphic illustration of the results of oral gavage testing in rats using salmon calcitonin with acetyl phenylalanine aldehyde, carbomethoxyPhe-Leu-OH, and acetyl-Phe-Leu-Leu-Arg aldehyde carriers.

Amino acids and amino acid derivatives, in modified form, may be used to deliver orally sensitive biologically-active agents, including, but not limited to, hormones such as calcitonin, insulin, and polysaccharides such as heparin, which would not be considered orally administrable for various reasons. Insulin, for example is sensitive to the denaturing conditions of the gastro-intestinal (GI) tract. Also, heparin, by virtue of its charge and hydrophilic nature, is not readily absorbed from the gastro-intestinal tract. In contrast to the modified amino acids and modified amino acid derivatives of the present invention, unmodified free amino acids do not provide protection against degradation in the GI tract for labile bioactive agents.

The compositions of the subject invention are useful for administering biologically-active agents to any animals such as birds; mammals, such as primates and particularly humans; and insects.

Other advantages provided by the present invention include the use of readily available and inexpensive starting materials in cost-effective methods for preparing and isolating modified amino acid derivatives. These methods are simple to perform and are amenable to industrial scale-up for commercial production.

Biologically-active agents suitable for use with carriers disclosed herein include, but are not limited to, peptides, and particularly small peptide hormones, which by themselves do not pass or only pass slowly through the gastro-intestinal mucosa and/or are susceptible to chemical cleavage by acids and enzymes in the gastro-intestinal tract; polysaccharides and particularly mixtures of muco-polysaccharides; carbohydrates; lipids; or any combination thereof. Examples include, but are not limited to, human growth hormone; bovine growth hormone; growth hormone releasing hormone; interferons; interleukin-I; insulin; heparin, and particularly low molecular weight heparin; calcitonin; erythropoietin; atrial naturetic factor; antigens; monoclonal antibodies; somatostatin; adrenocorticotropin; gonadotropin releasing hormone; oxytocin; vasopressin; cromolyn sodium (sodium or disodium cromoglycate); vancomycin; desferrioxamine (DFO); or any combination thereof.

Additionally the carriers of the present invention can be used to deliver other active agents such as pesticides and the like.

The term amino acid as used herein includes any carboxylic acid having at least one free amine group including naturally occurring and synthetic amino acids. The preferred amino acids are ∝-amino acids, and preferably are naturally occurring ∝-amino acids although non-α-amino acids are useful as well.

Poly amino acids as used herein refers to peptides or two or more amino acids linked by a bond formed by other groups which can be linked, e.g., an ester, anhydride or an anhydride linkage.

The term peptide is meant to include two or more amino acids joined by a peptide bond. Peptides can vary in length from dipeptides with 2 to poly peptides with several hundred amino acids. See *Chambers Biological Dictionary*, editor Peter M. B. Walker, Cambridge, England: Chambers Cambridge, 1989, page 215. The peptides most useful in the practice of the present invention include di-peptides, tri-peptides, tetra-peptides, and penta-peptides. The preferred peptides are di-peptides, tri-peptides. Peptides can be homo- or hetero-peptides and can include natural amino acids, synthetic amino acids, or any combination thereof.

The term amino acid derivatives and peptide derivatives as used herein are meant to include amino acid aldehydes or ketones and/or peptide aldehydes or ketones where the —COOH group has been converted to a ketone or aldehyde.

The terms modified amino acids, peptides, and derivatives thereof are meant to include amino acids, amino acid derivatives, peptides and peptide derivatives which have been modified as described below by acylating or sulfonating at least one free amine group, with an acylating or sulfonating agent which reacts with at least one of the free amine groups present.

The preferred naturally occurring amino acids for use in the present invention as amino acids or components of a peptide are alanine, arginine, asparagine, aspartic acid, citrulline, cysteine, cystine, glutamine, glycine, histidine, isoleucine, leucine, lysine, methionine, ornithine, phenylalanine, proline, serine, threonine, tryptophan, tyrosine, valine, hydroxy proline, γ-carboxyglutamate, or O-phosphoserine. The most preferred amino acids are arginine, leucine, lysine, phenylalanine, tyrosine and valine.

The preferred non-naturally occurring amino acids for use in the present invention as amino acids or components of a peptide are β-alanine, phenylglycine, α-aminobutyric acid, γ-amino butyric acid, 4-(4-aminophenyl)butyric acid, α-amino isobutyric acid, ε-aminocaproic acid, 7-aminoheptanoic acid, β-aspartic acid, aminobenzoic acid, (aminomethyl)benzoic acid, aminophenylacetic acid, aminohippuric acid, γ-glutamic acid, cysteine(ACM), ε-lysine, ε-lysine (A-Fmoc), methionine sulfone, norleucine, norvaline, ornithine, d-ornithine, p-nitrophenylalanine, hydroxy proline, and thioproline.

The amino acids useful in the practice of the subject invention have the formula:

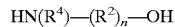

$R^2$ has the formula

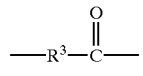

wherein $R^3$ is $C_1$ to $C_{24}$ alkyl, $C_1$ to $C_{24}$ alkenyl, phenyl, naphthyl, ($C_1$ to $C_{10}$ alkyl)-phenyl, ($C_1$ to $C_{10}$ alkenyl) phenyl, ($C_1$ to $C_{10}$ alkyl) naphthyl, ($C_1$ to $C_{10}$ alkenyl) naphthyl, phenyl ($C_1$ to $C_{10}$ alkyl), phenyl ($C_1$ to $C_{10}$ alkenyl), naphthyl($C_1$ to $C_{10}$ alkyl) and naphthyl ($C_1$ to $C_{10}$ alkenyl);

optionally $R^3$ is substituted with $C_1$ to $C_4$ alkyl, $C_1$ to $C_4$ alkenyl, $C_1$ to $C_4$ alkoxy, —OH, —SH and —$CO_2R^5$ or any combination thereof;

$R^5$ is hydrogen, $C_1$ to $C_4$ alkyl or $C_1$ to $C_4$ alkenyl;

$R^3$ is optionally interrupted by oxygen, nitrogen, sulfur or any combination thereof; and $R^4$ is hydrogen, $C_1$ to $C_4$ alkyl or $C_1$ to $C_4$ alkenyl.

The phenyl or naphthyl groups can be optionally substituted. Suitable but non-limiting examples of substitutents are $C_1$ to $C_6$ alkyl, $C_1$ to $C_6$ alkenyl, alkoxy having from 1 to 6 carbon atoms, hydroxy, thio, or $CO_2R^6$ wherein $R^6$ is hydrogen, $C_1$ to $C_6$ alkyl, $C_1$ to $C_6$ alkenyl.

The amino acid derivatives or peptide derivatives of the present invention can be readily prepared by reduction of amino acid esters or peptide esters with an appropriate reducing agent. For example, amino acid aldehydes or peptide aldehydes can be prepared as described in an article by R. Chen et al., *Biochemistry*, 1979, 18, 921–926. Amino acid or peptide ketones can be prepared by the procedure described in *Organic Syntheses, Col. Vol. IV*, Wiley, (1963), pages 5–6. Amino acids, peptides, amino acid esters, peptide esters, and other necessary reagents to prepare these derivatives are readily available from a number of commercial sources such as Aldrich Chemical Co. (Milwaukee, Wis., USA); Sigma Chemical Co. (St. Louis, Mo., USA); and Fluka Chemical Corp. (Ronkonkoma, N.Y., USA).

The amino acids and peptides are modified by acylating or sulfonating at least one free amine group, with an acylating or sulfonating agent which reacts with at least one of the free amine groups present. Suitable, but non-limiting, examples of agents useful for modifying amino acids or peptides useful in practicing the present invention include acylating and sulfonating agents having the formula

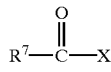

or $R^7$—$SO_2$—X wherein $R^7$ is alkyl or alkenyl, preferably having from 1 to 20 carbon atoms, or aromatic preferably having from 6 to 20 carbon atoms.

The $R^7$ group can be substituted or unsubstituted, The preferred substitutents include $C_1$ to $C_4$ alkyl, $C_1$ to $C_4$ alkenyl, $C_1$ to $C_4$ alkoxy, $CO_2R^8$ wherein $R^8$ is hydrogen, $C_1$ to $C_4$ alkyl or $C_1$ to $C_4$ alkenyl.

Preferably, $R^7$ is methyl, ethyl, phenyl, benzyl or naphthyl. More preferably, $R^7$ is phenyl, or acetyl. X is a leaving group. In a reaction in which the substrate molecule becomes cleaved, part of it (the part not containing the carbon) is usually called the leaving group. See *Advanced Organic Chemistry*, 2d edition, Jerry March, New York: McGraw-Hill Book (1977), page 187, Typical leaving groups include, but are not limited to, halogens such as chlorine, bromine and iodine.

Examples of the acylating and sulfonating agents for amino acids and peptides include, but are not limited to, acyl halides such as acetyl chloride, propyl chloride, benzoyl chloride, hippuryl chloride and the like; sulfonyl halides such as benzene sulfonyl chloride, and anhydrides, such as acetic anhydride, propyl anhydride, benzoic anhydride, hippuric anhydride and the like. The preferred acylating and sulfonating agents are benzoyl chloride, benzene sulfonyl chloride, and hippuryl chloride.

The modified acid compounds have the formula:

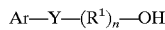

wherein Ar is a substituted or unsubstituted phenyl or naphthyl;

Y is

or —$SO_2$—, $R^1$ has the formula

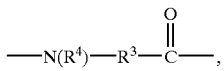

wherein:

$R^3$ is $C_1$ to $C_{24}$ alkyl, $C_1$ to $C_{24}$ alkenyl, phenyl, naphthyl, ($C_1$ to $C_{10}$ alkyl) phenyl, ($C_1$ to $C_{10}$ alkenyl) phenyl, ($C_1$ to $C_{10}$ alkyl) naphthyl, ($C_1$ to $C_{10}$ alkenyl) naphthyl, phenyl ($C_1$ to $C_{10}$ alkyl), phenyl ($C_1$ to $C_{10}$ alkenyl), naphthyl ($C_1$ to $C_{10}$ alkyl) and naphthyl ($C_1$ to $C_{10}$ alkenyl);

$R^3$ is optionally substituted with $C_1$ to $C_4$ alkyl, $C_1$ to $C_4$ alkenyl, $C_1$ to $C_4$ alkoxy, —OH, —SH and —$CO_2R^5$ or any combination thereof;

$R^5$ is hydrogen, $C_1$ to $C_4$ alkyl or $C_1$ to $C_4$ alkenyl;

$R^3$ is optionally interrupted by oxygen, nitrogen, sulfur or any combination thereof; and $R^4$ is hydrogen, $C_1$ to $C_4$ alkyl or $C_1$ to $C_4$ alkenyl.

The amino acid derivatives and peptide derivatives are modified by acylating at least one free amine group, with an acylating agent which reacts with at least one of the free amine groups present. Suitable, but non-limiting, examples of acylating agents useful for modifying amino acid derivatives and peptide derivatives useful in practicing the present invention include acid chloride acylating agents having the formula

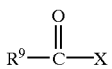

or wherein:

$R^9$ is alkyl or alkenyl, preferably having from 1 to 20 carbon atoms, cycloalkyl or cycloalkenyl, preferably having from 1 to 20 carbon atoms, or aromatic preferably having from 6 to 20 carbon atoms. The $R^9$ group can be substituted or unsubstituted, The preferred substituents include $C_1$ to $C_4$ alkyl, $C_1$ to $C_4$ alkenyl, $C_1$ to $C_4$ alkoxy, $CO_2R^{10}$ wherein $R^{10}$ is hydrogen, $C_1$ to $C_4$ alkyl or $C_1$ to $C_4$ alkenyl. Preferably, $R^9$ is methyl, ethyl, cyclohexyl, cyclopentyl, cycloheptyl, phenyl, benzyl or naphthyl. More preferably, $R^9$ is phenyl, cyclohexyl cyclopentyl, cycloheptyl, or acetyl. X is a leaving group. Typical leaving groups include, but are not limited to, halogens such as chlorine, bromine and iodine.

Examples of the acylating agents for amino acid derivatives and peptide derivatives include, but are not limited to, acyl halides such as acetyl chloride, propyl chloride, cyclohexanoyl chloride, cyclopentanoyl chloride, and cycloheptanoyl chloride, benzoyl chloride, hippuryl chloride and the like; and anhydrides, such as acetic anhydride, propyl anhydride, cyclohexanoic anhydride, benzoic anhydride, hippuric anhydride and the like. The preferred acylating agents are benzoyl chloride, benzene sulfonyl chloride, hippuryl chloride, acetyl chloride, cyclohexanoyl chloride, cyclopentanoyl chloride, and cycloheptanoyl chloride.

The amine groups can also be modified by the reaction of a carboxylic acid with coupling agents such as dicyclohexylcarbodiimide and the like. In a peptide one or more of the amino acids may be derivatized (an aldehyde or a ketone) and/or modified (acylated).

Also suitable as a carrier alone or in combination with the modified amino acid or peptide derivatives are the carbomethoxy modified amino acids carboxy-methyl-phenylalanine-leucine, 2-carboxy-3-phenylpropionyl-leucine, 2-benzylsuccinic acid and an actinonin. The actinonin compounds include actinonin or epiactinonin and derivatives thereof. These compounds have the formulas below:

Actinonin

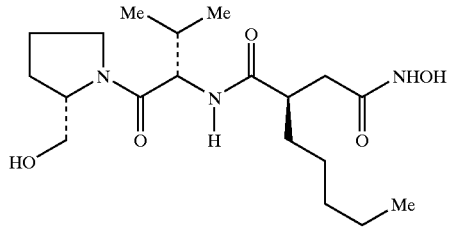

Epiactinonin

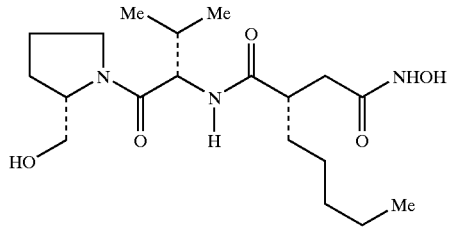

Derivatives of these compounds are disclosed in U.S. Pat. No. 5,206,384.

Actinonin derivatives have the formula:

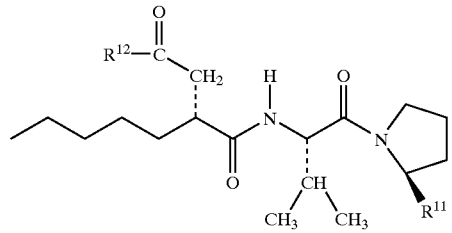

wherein $R^{11}$ is sulfoxymethyl or carboxyl or a substituted carboxy group selected from carboxamide, hydroxyaminocarbonyl and alkoxycarbonyl groups; and $R^{12}$ is hydroxyl, alkoxy, hydroxyamino or sulfoxyamino group.

The modified amino acid derivatives or peptide derivatives can be readily prepared and modified by methods known to those skilled in the art. For example, the modified amino acid derivatives of the present invention may be prepared by reacting a single amino acid derivative or peptide derivative or mixtures of two or more amino acid or peptide derivatives, with an acylating agent or an amine modifying agent which reacts with free amino moieties present in the derivatives to form amides. The amino acid or peptide can be modified and subsequently derivatized, derivatized and subsequently modified, or simultaneously modified and derivatized. Protecting groups may be used to avoid unwanted side reactions as would be known to those skilled in the art.

The modified amino acids and modified amino acid derivatives of the present invention may also be prepared by reacting single amino acids, mixtures of two or more kinds of amino acids, or amino acid esters with an amine modifying agent which reacts with free amino moieties present in the amino acids to form amides or sulfonamides. Amino acids and amino acid esters are readily available from a number of commercial sources such as Aldrich Chemical Co. (Milwaukee, Wis., U.S.A.); Sigma Chemical Co. (St. Louis, Mo., USA); and Fluka Chemical Corp. (Ronkonkoma, N.Y., USA).

For example, the amino acids can be dissolved in aqueous alkaline solution of a metal hydroxide, e.g., sodium or potassium hydroxide, and heated at a temperature ranging between about 5° C. and about 70° C., preferably between about 10° C. and about 40° C., for a period ranging between about 1 hour and about 4 hours, preferably about 2.5 hours. The amount of alkali employed per equivalent of $NH_2$ groups in the amino acids generally ranges between about 1.25 and about 3 mmole, preferably between about 1.5 and about 2.25 mmole per equivalent of $NH_2$. The pH of the solution generally ranges between about 8 and about 13, preferably ranging between about 10 and about 12.

Thereafter, an amino modifying agent is added to the amino acid solution while stirring. The temperature of the mixture is maintained at a temperature generally ranging between about 5° C. and about 70° C., preferably between about 10° C. and about 40° C., for a period ranging between about 1 and about 4 hours. The amount of amino modifying agent employed in relation to the quantity of amino acids is based on the moles of total free $NH_2$ in the amino acids. In general, the amino modifying agent is employed in an amount ranging between about 0.5 and about 2.5 mole equivalents, preferably between about 0.75 and about 1.25 equivalents, per molar equivalent of total $NH_2$ groups in the amino acids.

The reaction is quenched by adjusting the pH of the mixture with a suitable acid, e.g., concentrated hydrochloric acid, until the pH reaches between about 2 and about 3. The mixture separates on standing at room temperature to form a transparent upper layer and a white or off-white precipitate. The upper layer is discarded and modified amino acids are collected from the lower layer by filtration or decantation. The crude modified amino acids are then dissolved in water at a pH ranging between about 9 and about 13, preferably between about 11 and about 13. Insoluble materials are removed by filtration and the filtrate is dried in vacuo. The yield of modified amino acids generally ranges between about 30 and about 60%, and usually about 45%.

If desired, amino acid esters, such as, for example methyl or ethyl esters of amino acids, may be used to prepare the modified amino acids of the invention. The amino acid esters, dissolved in a suitable organic solvent such as dimethylformamide or pyridine, are reacted with the amino modifying agent at a temperature ranging between about 5° C. and about 70° C., preferably about 25° C., for a period ranging between about 7 and about 24 hours. The amount of amino modifying agents used relative to the amino acid esters are the same as described above for amino acids.

Thereafter, the reaction solvent is removed under negative pressure and the ester functionality is removed by hydrolyzing the modified amino acid ester with a suitable alkaline solution, e.g. 1N sodium hydroxide, at a temperature ranging between about 50° C. and about 80° C., preferably about 70° C., for a period of time sufficient to hydrolyze off the ester group and form the modified amino acid having a free carboxyl group. The hydrolysis mixture is then cooled to room temperature and acidified, e.g. aqueous 25% hydrochloric acid solution, to a pH ranging between about 2 and about 2.5. The modified amino acid precipitates out of solution and is recovered by conventional means such as filtration or decantation.

The modified amino acids may be purified by recrystallization or by fractionation on solid column supports. Suitable recrystallization solvent systems include acetonitrile, methanol and tetrahydrofuran. Fractionation may be performed on a suitable solid column supports such as alumina, using methanol/n-propanol mixtures as the mobile phase; reverse phase column supports using trifluoroacetic acid/acetonitrile mixtures as the mobile phase; and ion exchange chromatography using water as the mobile phase. When anion exchange chromatography is performed, a subsequent 0–500 mM sodium chloride gradient is employed. The modified amino acids may also be purified by extraction with a lower alcohol such as methanol, butanol, or isopropanol to remove low molecular weight non-sphere making material.

Suitable modified amino acid derivatives include, but are not limited to, N-cyclohexanoyl-Phe aldehyde, N-acetyl-Phe-aldehyde, N-acetyl-Tyr ketone, N-acetyl-Lys ketone and N-acetyl-Leu ketone. Special mention is made of the modified amino acid derivative N-cyclohexanoyl phenylalanine aldehyde.

Special mention is made of compositions in which the biologically-active agent includes, calcitonin and the carrier includes acetyl phenylalanine aldehyde, carbomethoxy phenylalanylleucine and acetyl-Phe-Leu-Leu aldehyde.

Special mention is also made of a composition which includes 1.5 μg/ml of the biologically-active agent calcitonin and the carrier includes 132 mg/ml of acetyl phenylalanine, 33 mg/ml of carbomethoxy phenylalanylleucine, and 25 mg/ml of acetyl-Phe-Leu-Leu-Arg aldehyde.

In one embodiment, the modified and/or modified derivatized amino acids may be used directly as a delivery carrier by simply mixing the carrier with the active ingredient prior to administration. In an alternative embodiment, the modified amino acids may be used to form microspheres containing the active agent. The modified and/or modified derivatized amino acids of the invention are particularly useful for the oral administration of certain pharmacological agents, e.g., small peptide hormones, which, by themselves, do not pass or only pass slowly through the gastro-intestinal mucosa and/or are susceptible to chemical cleavage by acids and enzymes in the gastro-intestinal tract.

If the modified amino acids are to be converted into microspheres, the mixture is optionally heated to a temperature ranging between about 20 and about 50° C., preferably about 40° C., until the modified amino acid(s) dissolve. The final solution contains between from about 1 mg and about 2000 mg of modified amino acids per mL of solution, preferably between about 1 and about 500 mg per mL. The concentration of active agent in the final solution varies and is dependent on the required dosage for treatment. When necessary, the exact concentration can be determined by, for example, reverse phase HPLC analysis.

When the modified amino acids are used to prepare microspheres, another useful procedure is as follows: Modified amino acids are dissolved in deionized water at a concentration ranging between about 75 and about 200 mg/ml, preferably about 100 mg/ml at a temperature between about 25° C. and about 60° C., preferably about 40° C. Particulate matter remaining in the solution may be removed by conventional means such as filtration.

Thereafter, the modified amino acid solution, maintained at a temperature of about 40° C., is mixed 1:1 (V/V) with an aqueous acid solution (also at about 40° C.) having an acid concentration ranging between about 0.05 N and about 2 N, preferably about 1.7 N. The resulting mixture is further incubated at 40° C. for a period of time effective for microsphere formation, as observed by light microscopy. In practicing this invention, the preferred order of addition is to add the modified amino acid solution to the aqueous acid solution.

Suitable acids for microsphere formation include any acid which does not (a) adversely effect the modified amino acids, e.g., initiate or propagate chemical decomposition;

(b) interfere with microsphere formation;

(c) interfere with microsphere encapsulation of the cargo; and (d) adversely interact with the cargo.

Preferred acids for use in this invention include acetic acid, citric acid, hydrochloric acid, phosphoric acid, malic acid and maleic acid.

In practicing the invention, a microsphere stabilizing additive may be incorporated into the aqueous acid solution or into the amino acid solution prior to the microsphere formation process. With some drugs the presence of such additives promotes the stability and/or dispersibility of the microspheres in solution.

The stabilizing additives may be employed at a concentration ranging between about 0.1 and 5% (w/v), preferably about 0.5% (w/v). Suitable, but non-limiting, examples of microsphere stabilizing additives include gum acacia, gelatin, methyl cellulose, polyethylene glycol, and polylysine. The preferred stabilizing additives are gum acacia, gelatin and methyl cellulose.

Under the above conditions, the modified amino acid molecules form hollow or solid matrix type microspheres wherein the cargo is distributed in a carrier matrix or capsule type microspheres encapsulating liquid or solid cargo. If the modified amino acid microspheres are formed in the presence of a soluble material, e.g., a pharmaceutical agent in the aforementioned aqueous acid solution, this material will be encapsulated within the microspheres. In this way, one can encapsulate pharmacologically active materials such as peptides, proteins, and polysaccharides as well as charged organic molecules, e.g., antimicrobial agents, which normally have poor bioavailability by the oral route. The amount of pharmaceutical agent which may be encapsulated by the microsphere is dependent on a number of factors which include the concentration of agent in the encapsulating solution, as well as the affinity of the cargo for the carrier.

The modified amino acid microspheres of the invention are pharmacologically harmless and do not alter the physiological and biological properties of the active agent. Furthermore, the encapsulation process does not alter the pharmacological properties of the active agent Any pharmacological agent can be encapsulated within the amino acid microspheres. The system is particularly advantageous for delivering chemical or biological agents which otherwise would be destroyed or rendered less effective by conditions encountered within the body of the animal to which it is administered, before the microsphere reaches its target zone (i.e., the area in which the contents of the microsphere are to be released) and pharmacological agents which are poorly absorbed in the gastro-intestinal tract. The target zones can vary depending upon the drug employed.

The particle size of the microsphere plays an important role in determining release of the active agent in the targeted area of the gastro-intestinal tract. The preferred microspheres have diameters between about $\leq 0.1$ microns and about 10 microns, preferably between about 0.5 microns and about 5 microns. The microspheres are sufficiently small to release effectively the active agent at the targeted area within the gastrointestinal tract. Small microspheres can also be administered parenterally by being suspended in an appropriate carrier fluid (e.g., isotonic saline) and injected directly into the circulatory system, intramuscularly or subcutaneously. The mode of administration selected will vary, of course, depending upon the requirement of the active agent being administered. Large amino acid microspheres (>50 microns) tend to be less effective as oral delivery systems.

The size of the microspheres formed by contacting modified amino acid with water or an aqueous solution containing active agents can be controlled by manipulating a variety of physical or chemical parameters, such as the pH, osmolarity or ionic strength of the encapsulating solution, size of the ions in solution and by the choice of acid used in the encapsulating process.

Typically, the pharmacological compositions of the present invention are prepared by mixing an aqueous solution of the carrier with an aqueous solution of the active ingredient, just prior to administration. Alternatively, the carrier and biologically active ingredient can be admixed during the manufacturing process. The solutions may optionally contain additives such as phosphate buffer salts, citric acid, acetic acid, gelatin and gum acacia.

In practicing the invention, stabilizing additives may be incorporated into the carrier solution. With some drugs, the presence of such additives promotes the stability and dispersibility of the agent in solution.

The stabilizing additives may be employed at a concentration ranging between about 0.1 and 5% (W/V), preferably about 0.5% (W/V). Suitable, but non-limiting, examples of stabilizing additives include gum acacia, gelatin, methyl cellulose, polyethylene glycol, and polylysine. The preferred stabilizing additives are gum acacia, gelatin and methyl cellulose.

The amount of active agent in the composition typically is a pharmacologically or biologically effective amount. However, the amount can be less than a pharmacologically or biologically effective amount when the composition is used in a dosage unit form, such as a capsule, a tablet or a liquid, because the dosage unit form may contain a multiplicity of carrier/biologically-active agent compositions or may contain a divided pharmacologically or biologically effective amount. The total effective amounts will be administered by cumulative units containing in total pharmacologically or biologically active amounts of biologically-active agent.

The total amount of biologically-active agent to be used can be determined by those skilled in the art. However, it has surprisingly been found that with certain biologically-active agents, such as calcitonin, the use of the presently disclosed carriers provides extremely efficient delivery. Therefore, lower amounts of biologically-active agent than those used in prior dosage unit forms or delivery systems can be administered to the subject, while still achieving the same blood levels and therapeutic effects.

The amount of carrier in the present composition is a delivery effective amount and can be determined for any particular carrier or biologically-active agent by methods known to those skilled in the art.

Dosage unit forms can also include any of excipients; diluents; disintegrants; lubricants; plasticizers; colorants; and dosing vehicles, including, but not limited to water, 1,2-propane diol, ethanol, olive oil, or any combination thereof.

Administration of the present compositions or dosage unit forms is oral or by intraduodenal injection.

EXAMPLES

The invention will now be illustrated in the following non-limiting examples which are illustrative of the invention but are not intended to limit the scope of the invention.

Example 1

Preparation of N-Cyclohexanoylphenylalanine Aldehyde

Phenylalanine methyl ester (1 g., 0.0046 moles) was dissolved in pyridine 5 mL. Cyclohexanoyl chloride (0.62 mL) was added and the mixture was stirred for 2 hours. The reaction mixture was poured onto hydrochloric acid (1N) and crushed ice. The aqueous mixture was extracted twice with toluene. The combined toluene extracts were concentrated in vacuo to give 1.1 g of crude N-cyclohexanoylphenylalanine methyl ester.

N-Cyclohexanoylphenylalanine methyl ester (0.5 g) was dissolved in ethylene glycol dimethyl ether (20 mL). The solution was cooled to −70° C. and diisobutylaluminum hydride (2.04 mL of a 1.5M solution in toluene) was added. The resulting reaction mixture was stirred at −70° C. for 2 hours. The reaction was quenched by dropwise addition of 2N hydrochloric acid. The mixture was extracted with cold ethyl acetate. The ethyl acetate solution was washed with brine and dried over sodium sulfate. Concentration in vacuo furnished a white solid which was purified by silica gel chromatography. $^1$H NMR(300 MHz, DMSO-d6): 9.5 (s, 1H), 8.2 (d, 1H), 7.2 (m, 5H), 4.2 (m, 1H), 3.2 (d, 1H), 2.7 (d, 1H), 2.1 (m, 1H), 1.6 (br. m, 4H), 1.2 (br. m, 6H).

IR (KBr): 3300, 3050, 2900, 2850, 2800, 1700, 1600, 1500 cm-$^1$. Mass Spec.: M+1 m/e 261.

Example 2

Preparation of N-Acetylphenylalanine Aldehyde

N-Acetylphenylalanine methyl ester (4.2 g, 19 mmol) was dissolved in ethylene glycol dimethyl ether. The solution was cooled to −70° C. and diisobutylaluminum hydride (25.3 mL of a 1.5M solution in toluene, 39 mmol) was added. The resulting reaction mixture was stirred at −70° C. for 2 hours. The reaction was quenched by addition of 2N hydrochloric acid. The mixture was extracted 4 times with cold ethyl acetate and 4 times with toluene. The extracts were combined, washed with brine and dried over magnesium sulfate. Concentration in vacuo followed by silica gel chromatography furnished 2.7 g of a white solid. The NMR was identical to that reported in the literature, *Biochemistry*, 1979, 18, 921–926.

Example 3

Preparation of 3-Acetamido-4-(p-Hydroxy)Phenyl-2-Butanone (N-Acetyltyrosinone)

A mixture of tyrosine (28.9 g, 16 mmol), acetic anhydride (97.9 g,96 mmol) and pyridine (35 g, 16 mmol) were heated to 100° C. for 1 hour. The reaction mixture was concentrated in vacuo to furnish a yellow oil. The oil was distilled at reduced pressure to furnish 29.9 g or an oil.

$^1$H NMR (DMSO-d6): NMR (d6-DMSO); 8.2 (d, 1H), 7.3 (d, 2H), 7.0 (d, 2H), 4.4 (m, 1H), 3.1 (dd, 1H), 2.7 (dd, 1H), 2.3 (s, 3H), 1.8 (s, 3H).

Example 4

Preparation of 3-Acetamido-7-Amino-2-Butanone (N-Acetyllysinone)

Following the procedure of Example 3 lysine was converted to N-acetyllysinone.

$^1$H NMR (DMSO-d6): 8.1 (d, 1H), 7.8 (br.m. 1H), 4.1 (m, 1H), 3.0 (m, 2H), 2.0 (s, 3H), 1.9 (s, 3H) and 1.3 (br.m, 6H).

Example 5

Preparation of 3-Acetamido-5-Methyl-2-Butanone (N-Acetylleucinone)

Following the procedure of Example 3 leucine was converted to N-acetylleucinone.

$^1$H NMR (DMSO-d6): 8.1 (d, 1H), 4.2 (m, 1H), 2.0 (s, 3H), 1.8 (s, 3H), 0.8 (d, 6H).

Example 6

Modification of 4-(4-Aminophenyl)Butyric Acid Using Benzene Sulfonyl Chloride 4-(4-Aminophenyl)butyric acid, (20 g 0.11 moles) was dissolved in 110 mL of aqueous 2N sodium hydroxide solution. After stirring for about 5 minutes at room temperature, benzene sulfonyl chloride (14.2 mL, 0.11 moles) was added dropwise into the amino acid solution over a 15 minute period. After stirring for about 3 hours at room temperature the mixture was acidified to pH 2 by addition of hydrochloric acid. This furnished a light brown precipitate which was isolated by filtration. The precipitate was washed with warm water and dried. The yield of 4-(phenyl-sulfonamido)4-phenylbutyric acid was 24.3 g (69%). The melting point was 123–25° C.

If necessary, the modified amino acids can be purified by recrystallization and/or chromatography.

Example 7

Modification of 4-Aminobenzoic Acid Using Benzene Sulfonyl Chloride

Following the procedure of Example 6 4-aminobenzoic acid was converted to 4-(phenylsulfonamido)benzoic acid.

Example 8

Modification of 4-Aminophenylacetic Acid, 4-Aminohippuric Acid, and 4-Aminomethylbenzoic Acid Using Benzene Sulfonyl Chloride Following the procedure of Example 6, 4-aminophenylacetic acid, 4-aminohippuric acid, and 4-amino-methylbenzoic acid were converted to 4-(phenylsulfonamido)-phenylacetic acid, 4-(phenylsulfonamido)hippuric acid, and 4-(phenylsulfonamidomethyl)benzoic acid respectively.

Example 9

Modification of Amino Acids with Benzene Sulfonyl Chloride

A mixture of sixteen amino acids were prepared prior to chemical modification. The constituents of the mixture are summarized in Table 1. 65 grams of the amino acid mixture (total concentration of [–NH$_2$] groups=0.61 moles) was dissolved in 760 mL of 1N sodium hydroxide solution (0.7625 equivalents) at room temperature. After stirring for 20 minutes, benzene sulfonyl chloride (78 ml, 1 eq.) was added over a 20 minute period. The reaction mixture was then stirred for 2.5 hours, without heating. As some precipitation had occurred, additional NaOH solution (2N) was added to the solution until it reached pH 9.3. The reaction mixture stirred overnight at room temperature. Thereafter, the mixture was acidified using dilute hydrochloric acid (38%, 1:4) and a cream colored material precipitated out. The resulting precipitate was isolated by decantation and dissolved in sodium hydroxide (2N). This solution was then reduced in vacuo to give a yellow solid, which was dried on the lyophilizer.

TABLE 1

Amino Acid Composition

| Amino Acid | Weight (g) | % of Total Weight | No. of moles of each Amino Acid (× 10$^{-2}$) | No. of Moles of - [—NH$_2$] |
|---|---|---|---|---|
| Thr | 2.47 | 3.8 | 2.07 | 2.07 |
| Ser | 2.25 | 3.46 | 2.1 | 2.1 |
| Ala | 4.61 | 7.1 | 5.17 | 5.17 |
| Val | 4.39 | 6.76 | 3.75 | 3.75 |
| Met | 0.53 | 0.82 | 0.35 | 0.35 |
| Ile | 2.47 | 3.8 | 0.36 | 0.36 |
| Leu | 3.86 | 5.94 | 2.95 | 2.95 |
| Tyr | 1.03 | 1.58 | 0.56 | 0.56 |
| Phe | 4.39 | 6.76 | 0.27 | 0.27 |
| His | 2.47 | 3.8 | 1.6 | 3.2 |
| Lys | 4.94 | 7.6 | 3.4 | 6.8 |
| Arg | 5.13 | 7.9 | 2.95 | 5.90 |
| Glutamine | 9.87 | 15.18 | 6.76 | 13.42 |
| Glutamic Acid | 9.87 | 15.18 | 6.70 | 6.70 |
| Asparagine | 3.32 | 5.11 | 2.51 | 5.02 |
| Aspartic Acid | 3.32 | 5.11 | 2.50 | 2.50 |

Example 10

Modification of a Mixture of Five Amino Acids Using Benzene Sulfonyl Chloride An 86.1 g (0.85 moles of NH$_2$) mixture of amino acids (see Table 2) was dissolved in 643 mL (1.5 eq.) of aqueous 2N sodium hydroxide solution. After stirring for 30 minutes at room temperature, benzene sulfonyl chloride (108 mL, 0.86 moles) was added portionwise into the amino acid solution over a 15 minute period. After stirring for 2.5 hours at room temperature, the pH of the reaction mixture (pH 5) was adjusted to pH 9 with additional 2N sodium hydroxide solution. The reaction mixture stirred overnight at room temperature. Thereafter, the pH of the reaction mixture was adjusted to pH 2.5 by addition of dilute aqueous hydrochloric acid solution (4:1, H$_2$O:HCl) and a precipitate of modified amino acids formed. The upper layer was discarded and the resulting yellow precipitate was isolated by decantation, washed with water and dissolved in 2N sodium hydroxide (2N). The solution was reduced in vacuo to give a yellow solid which was lyophilized overnight. The yield of crude modified amino acid was 137.9 g.

TABLE 2

| Amino Acid | Moles of Amino Acid (× 10$^{-2}$) | Moles of [—NH$_2$] × 10$^{-2}$ |
|---|---|---|
| Valine | 7.5 | 7.5 |
| Leucine | 10.7 | 10.5 |
| Phenylalanine | 13.4 | 13.4 |
| Lysine | 21.0 | 42.0 |
| Arginine | 6.0 | 12.0 |

Example 11

Modification of a Mixture of Five Amino Acids Using Benzoyl Chloride

An 86 g (0.85 moles of NH$_2$) mixture of amino acids (see Table 2 in Example 10) was dissolved in 637 mL (1.5 eq.) of aqueous 2N sodium hydroxide solution. After stirring for 10 minutes at room temperature, benzoyl chloride (99 mL, 0.85 moles) was added portionwise into the amino acid solution over a 10 minute period. After stirring for 2.5 hours at room temperature, the pH of the reaction mixture (pH 12) was adjusted to pH 2.5 using dilute hydrochloric acid (4:1, H$_2$O:HCl) and a precipitate of modified amino acids formed. After settling for 1 hour, the resulting precipitate was isolated by decantation, washed with water and dissolved in sodium hydroxide (2N). This solution was then reduced in vacuo to give crude modified amino acids as a white solid (220.5 g).

Example 12

Modification of L-Valine Using Benzene Sulfonyl Chloride

L-Valine (50 g, 0.43 mol) was dissolved in 376 mL (0.75 eq.) of aqueous 2N sodium hydroxide by stirring at room temperature for 10 minutes. Benzene sulfonyl chloride (68.7 mL, 0.38 mol, 1.25 eq.) was then added to the amino acid solution over a 20 minute period at room temperature. After stirring for 2 hours at room temperature, a precipitate appeared. The precipitate was dissolved by adding 200 mL of additional 2N sodium hydroxide solution. After stirring for an additional 30 minutes, dilute aqueous hydrochloric acid solution (4:1, $H_2O$:HCl) was added until the pH of the reaction mixture reached 2.6. A precipitate of modified amino acids formed and was recovered by decantation. This material was dissolved in 2N sodium hydroxide and dried in vacuo to give a white solid. Yield of crude modified amino acids=84.6 g, 77%).

Example 13

Modification of Phenylalanine Methyl Ester Using Hippuryl Chloride

L-Phenylalanine Methyl Ester Hydrochloride (15 g, 0.084 mole) was dissolved in dimethylformamide (DMF) (100 mL) and to this was added pyridine (30 mL). A solution of hippuryl chloride (16.6 g, 0084 moles in 100 mL DMF) was immediately added to the amino acid ester solution in two portions. The reaction mixture was stirred at room temperature overnight. The reaction mixture was then reduced in vacuo and dissolved in 1N aqueous sodium hydroxide. The solution was heated at 70° C. for 3 hours in order to hydrolyze the methyl ester to a free carboxyl group. Thereafter, the solution was acidified to pH 2.25 using dilute aqueous hydrochloric acid solution (1:3 HCl/$H_2O$). A gum-like precipitate formed and this was recovered and dissolved in 1N sodium hydroxide. The solution was reduced in vacuo to afford 18.6 g of crude modified amino acid product (Yield 18.6 g). After recrystallization from acetonitrile, pure modified phenylalanine (12 g) was recovered as a white powder. m.p. 223–225° C.

Example 14

Preparation of Dosing Solutions

In a test tube 568 mg of acetyl phenylalanine aldehyde, 132 mg of carbomethoxy phenylalanylleucine and 100 mg acetyl-Phe-Leu-Leu-Arg aldehyde were added to 2.9 ml of 15% ethanol. The solution was stirred and NaOH (1.0 N) was added to raise the pH to 7.2. Water was added to bring the total volume to 4.0 mL. The sample had a carrier concentration of 200 mg/mL. Calcitonin (6 µg) was added to the solution. The total calcitonin concentration was 1.5 µg/mL.

Following a similar procedure a second solution having 668 mg of acetyl phenylalanine aldehyde and 132 mg of carbomethoxy phenylalanylleucine as the carrier composition and a third solution having as the carrier acetyl phenylalanine aldehyde. Each solution had a calcitonin concentration of 1.5 µg/mL.

Example 15

Preparation of Modified Amino Acid/Salmon Calcitonin Compositions (a) Preparation of Modified Amino Acid Microspheres Containing Encapsulated Salmon Calcitonin The modified amino acid mixture, prepared in accordance with Example 9, was dissolved at 40° C. in distilled water (pH 7.2) at a concentration of 100 mg/ml. The solution was then filtered with a 0.2 micron filter and the temperature was maintained at 40° C. Salmon calcitonin (Sandoz Corp., Basil, Switzerland) was dissolved in an aqueous solution of citric acid (1.7N) and gelatin (5%) at a concentration of 150 mg/ml. This solution was then heated to 40° C. The two heated solutions were then mixed 1:1 (v/v). The resulting microsphere suspension was then filtered with glass wool and centrifuged for 50 minutes at 1000 g. The pellet was resuspended with 0.85N citric acid to a volume 5 to 7 fold less than the original volume. Salmon calcitonin concentration of the resuspended pellet was determined by HPLC. Additional microspheres were made according to the above procedure without salmon calcitonin. These "empty microspheres" were used to dilute the encapsulated salmon calcitonin microsphere preparation to a final dosing suspension for animal testing.

(b) Preparation of a Soluble Modified Amino Acid Carrier/Salmon Calcitonin System A soluble amino acid dosing preparation containing salmon calcitonin was prepared by dissolving the modified amino acid material in distilled water (pH 8) to an appropriate concentration. The solution was heated to 40° C. and then filtered with a 0.2 micron filter. Salmon calcitonin, also dissolved in distilled water, was then added to the modified amino acid solution prior to oral administration.

Example 16

In Vivo Experiments in Rats

For each sample six fasted rats were anesthetized. The rats were administered, by oral gavage, one of the calcitonin/carrier dosages prepared in Example 15. The calcitonin concentration in each sample was 1.5 µg/ml. Each rat was administered a dosage of two (2) mL/kg each. Blood samples were collected serially from the tail artery. Serum calcium was determined by testing with a Demand™ Calcium Kit (available from Sigma Chemical Company, St. Louis, Mo., USA). The results of the test are illustrated in FIG. 1.

Example 17

Figure 2:
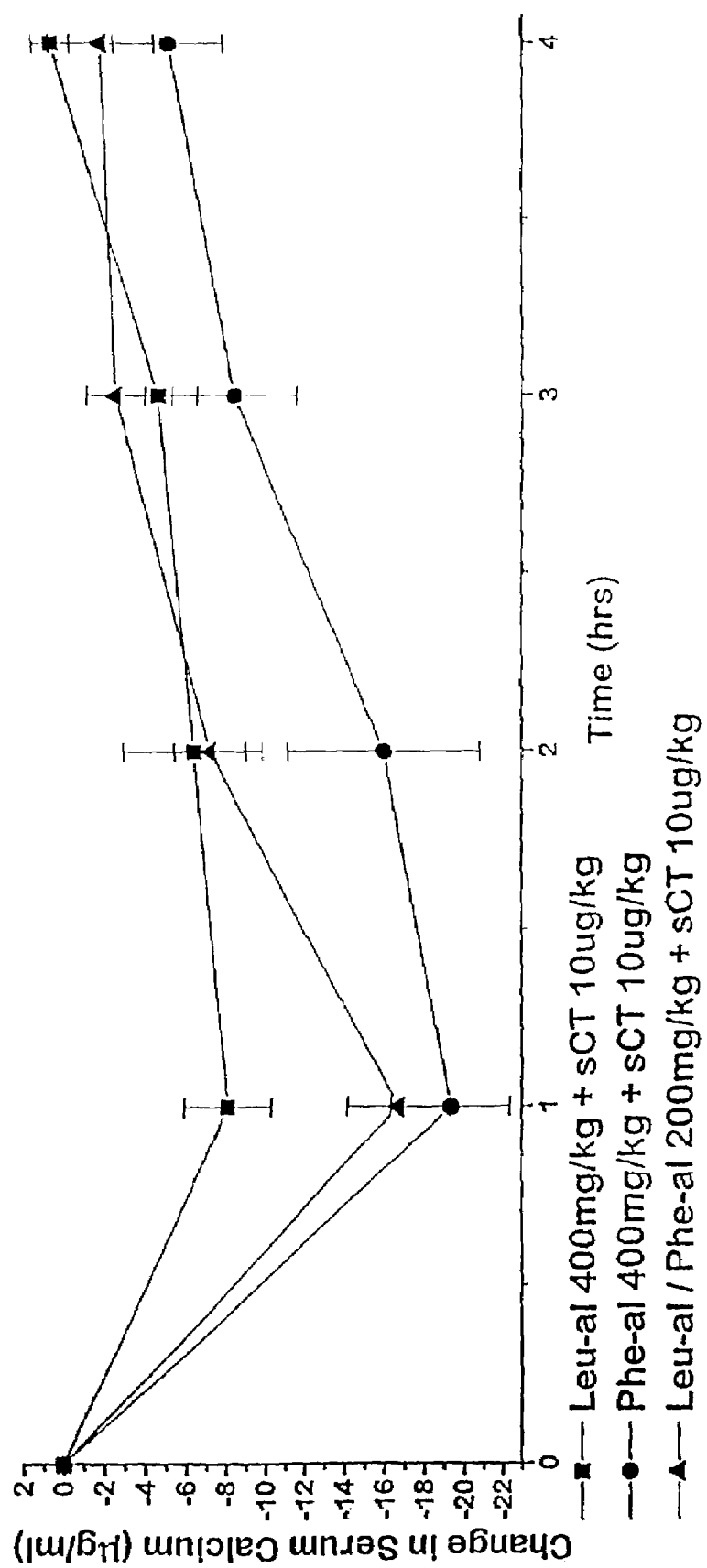
FIG. 2 is a graphic illustration of the results of oral gavage testing in rats using salmon calcitonin with acetylleucine aldehyde and acetylphenylalanine aldehyde carriers.

Three samples having 400 mg/kg of acetyl-Leu aldehyde and 10 µg/kg of calcitonin, 400 mg/kg of acetyl-Phe aldehyde and 10 µg/kg of calcitonin, 200 mg/kg of acetyl-Leu aldehyde, 200 mg/kg of acetyl-Phe aldehyde and 10 µg/kg of calcitonin, respectively were prepared. The samples were given to fasted rats as described in Example 16. The results of the test are illustrated graphically in FIG. 2.

Example 18

Figure 3:
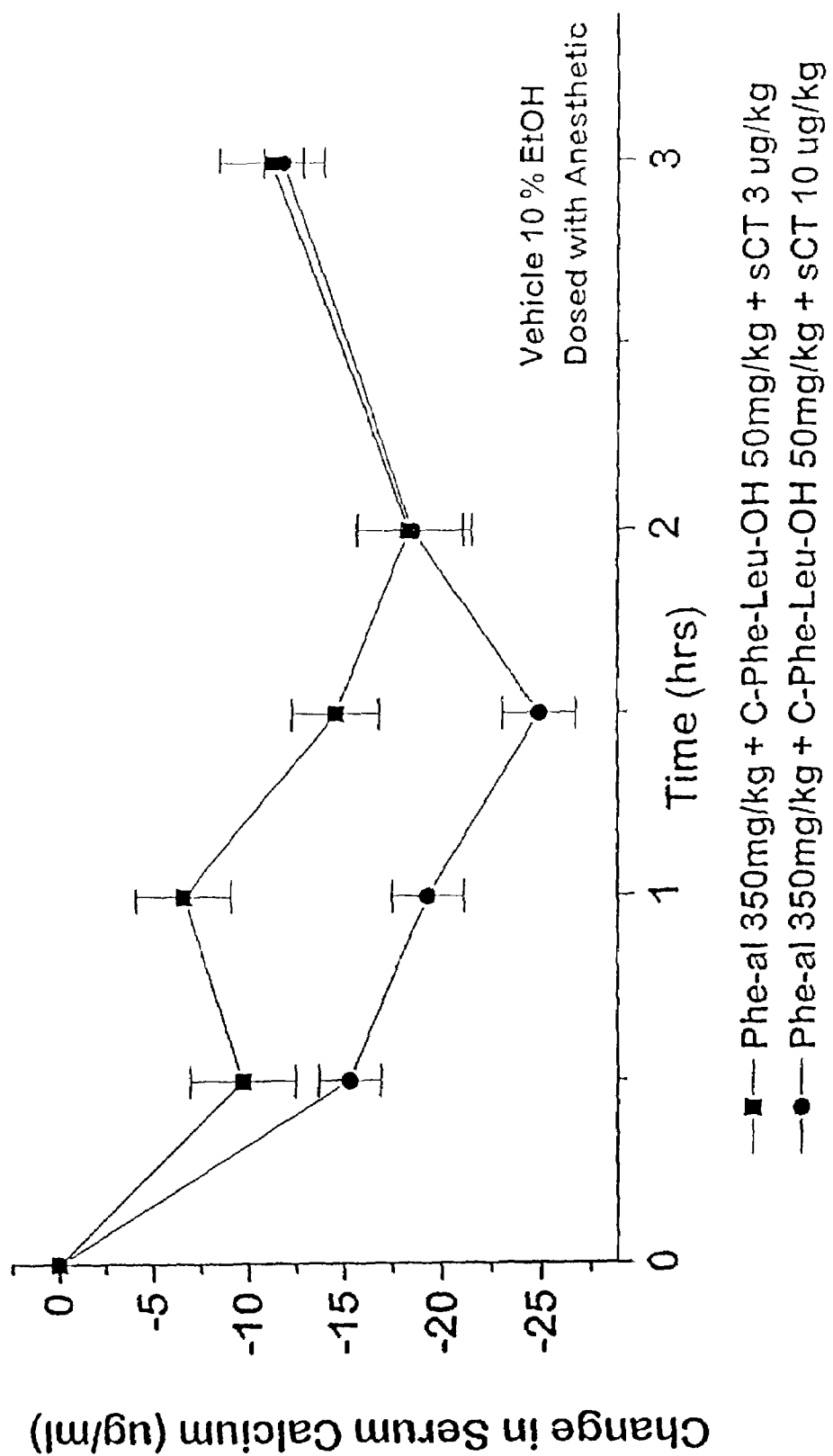
FIG. 3 is a graphic illustration of the results of oral gavage testing in rats using salmon calcitonin with acetylphenylalanine aldehyde and carbomethoxyPhe-Leu-OH carriers.

Two samples having 350 mg/kg of acetyl-Phe aldehyde, 50 mg/kg of carbomethoxy-Phe-Leu-OH and 3 µg/kg of calcitonin, 400 mg/kg of acetyl-Phe aldehyde, 50 mg/kg of carbomethoxy-Phe-Leu-OH and 10 µg/kg of calcitonin, respectively were prepared. The samples were given to fasted rats as described in Example 16. The results of the test are illustrated in FIG. 3.

Example 19

Figure 4:
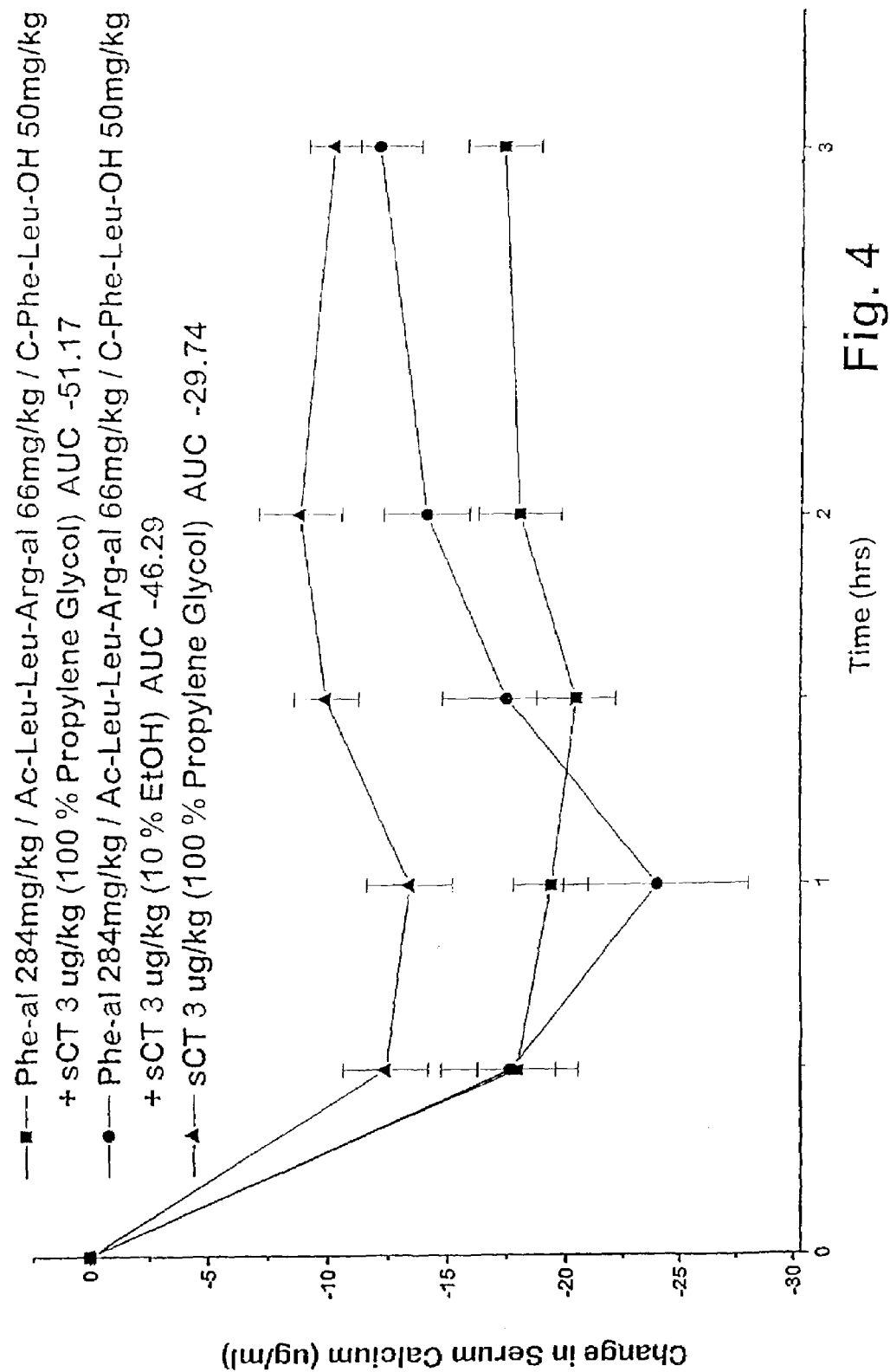
FIG. 4 is a graphic illustration of the results of oral gavage testing in rats using salmon calcitonin with acetylphenylalanine aldehyde, acetylLeu-Leu-Arg aldehyde and carbomethoxyPhe-Leu-OH carriers.

Three samples having 284 mg/kg of acetyl-Phe aldehyde and 66 mg/kg acetyl-Leu-Leu-Arg aldehyde, 50 mg/kg of carbomethoxy-Phe-Leu-OH and 3 µg/kg of calcitonin in propylene glycol, 284 mg/kg of acetyl-Phe aldehyde and 66 mg/kg acetyl-Leu-Leu-Arg aldehyde, 50 mg/kg of carbomethoxy-Phe-Leu-OH and 3 µg/kg of calcitonin and 3 µg/kg of calcitonin, in aqueous ethanol, respectively were prepared. The samples were given to fasted rats as described in Example 16. The results of the test are illustrated in FIG. 4.

Example 20

Figure 5:
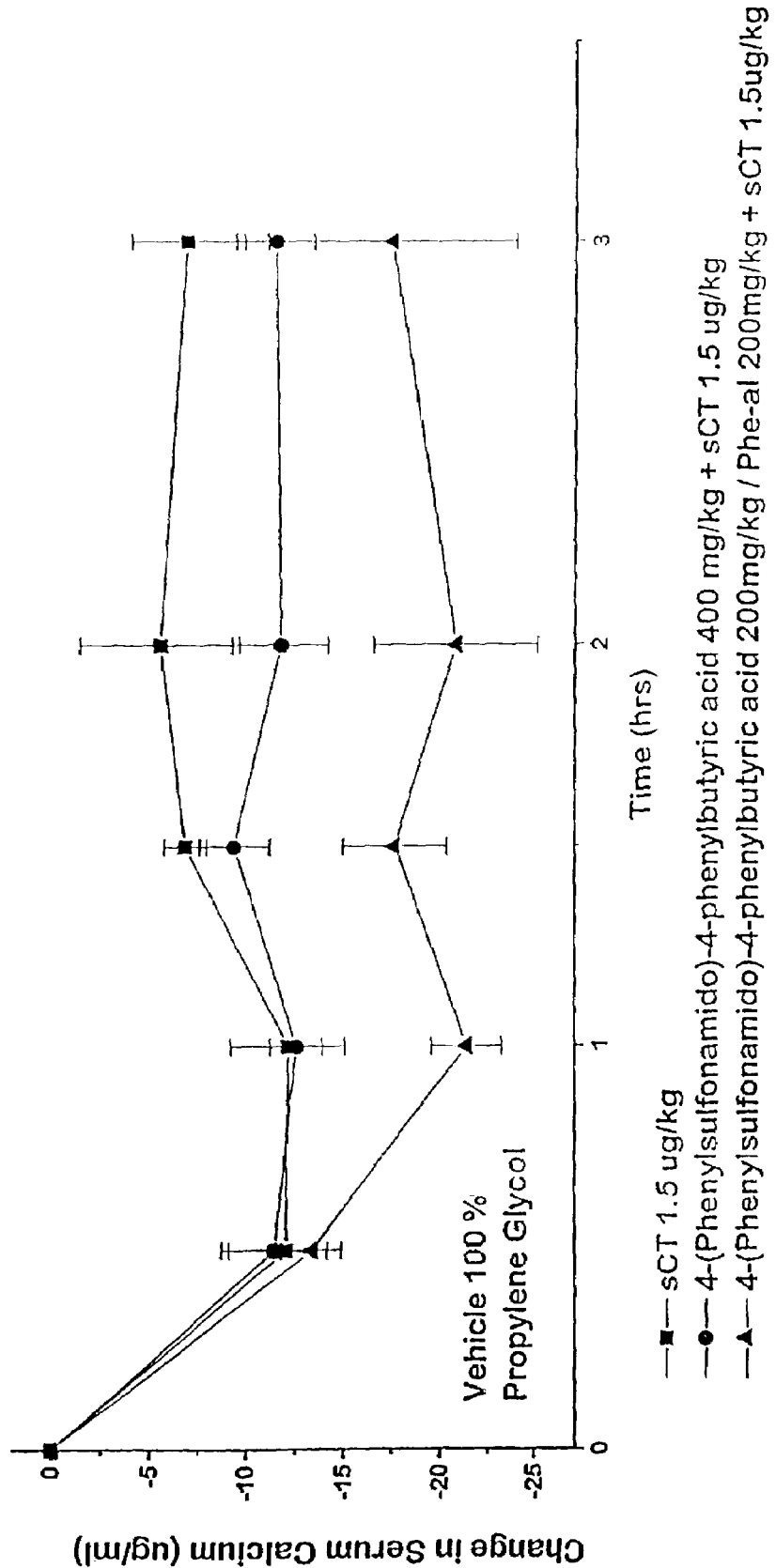
FIG. 5 is a graphic illustration of the results of intraduodenal injection testing in rats using salmon calcitonin with acetylphenylalanine aldehyde and 4-(phenylsulfonamido)-4-phenylbutyric acid carriers.

Three samples having 400 mg/kg of 4-(phenylsulfonamido)-4-phenylbutyric acid and 1.5 µg/kg of calcitonin in propylene glycol, 200 mg/kg of 4-(phenylsulfonamido)-4-phenylbutyric acid, 200 mg/kg of acetyl-Phe aldehyde and 1.5 µg/kg of calcitonin in aqueous ethanol, respectively were prepared. The samples were given to fasted rats by intraduodenal injection. The results of the test are illustrated in FIG. 5.

Example 21

Figure 6:
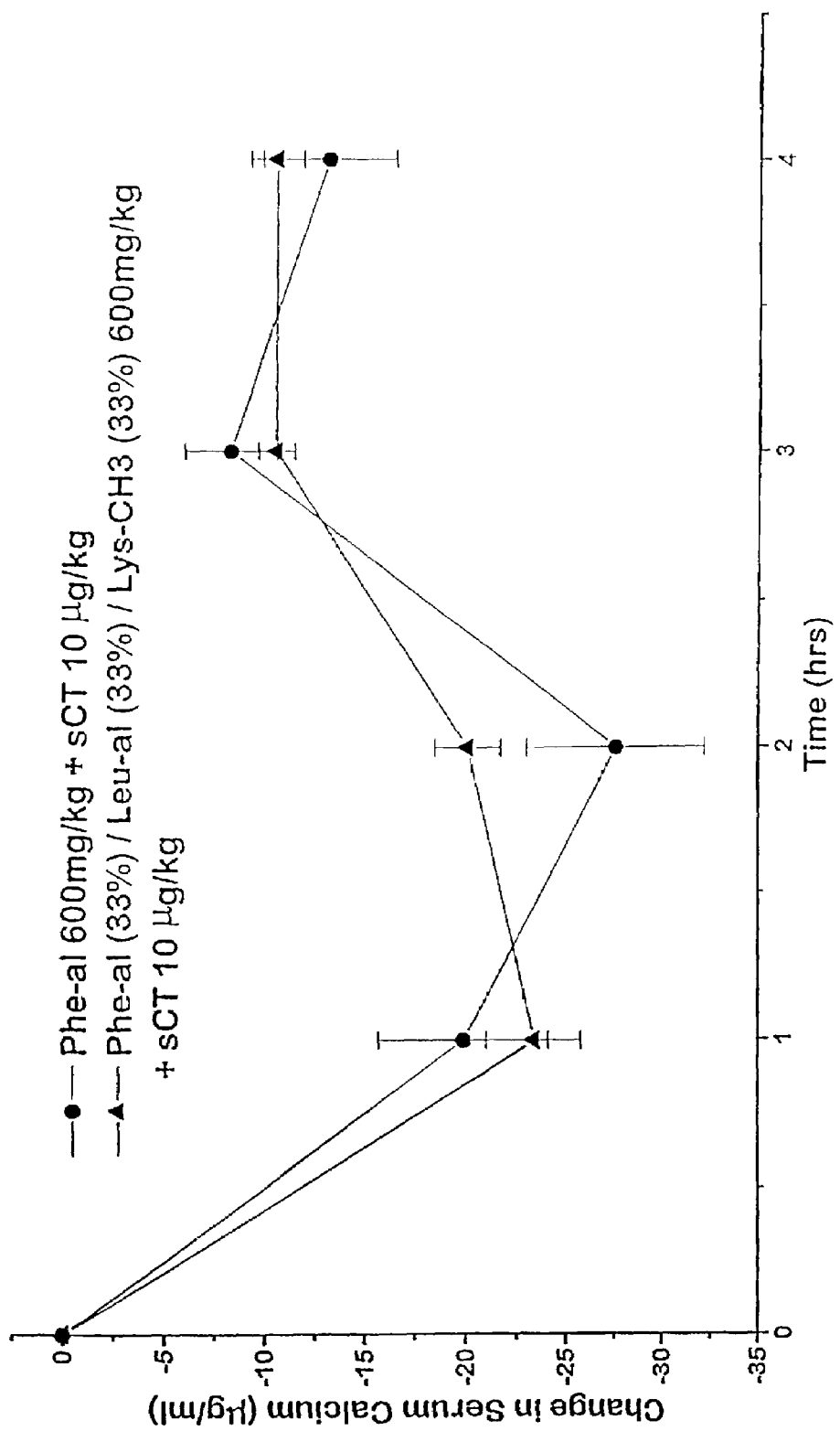
FIG. 6 is a graphic illustration of the results of oral gavage testing in rats using salmon calcitonin with acetylphenylalanine aldehyde, N-acetyllysinone, and acetyl-Leu aldehyde carriers.

Samples having 600 mg/kg of acetyl-Phe aldehyde and 10 µg/kg of calcitonin in aqueous ethanol, and 3 µg/kg of calcitonin, 200 mg/kg of acetyl-Phe aldehyde, 200 mg/kg N-acetyllysinone, 200 mg/kg acetyl-Leu aldehyde and 10 µg/kg of calcitonin were prepared. The samples were given to fasted rats as described in Example 16. The results of the test are illustrated in FIG. 6.

Example 22

Figure 7:
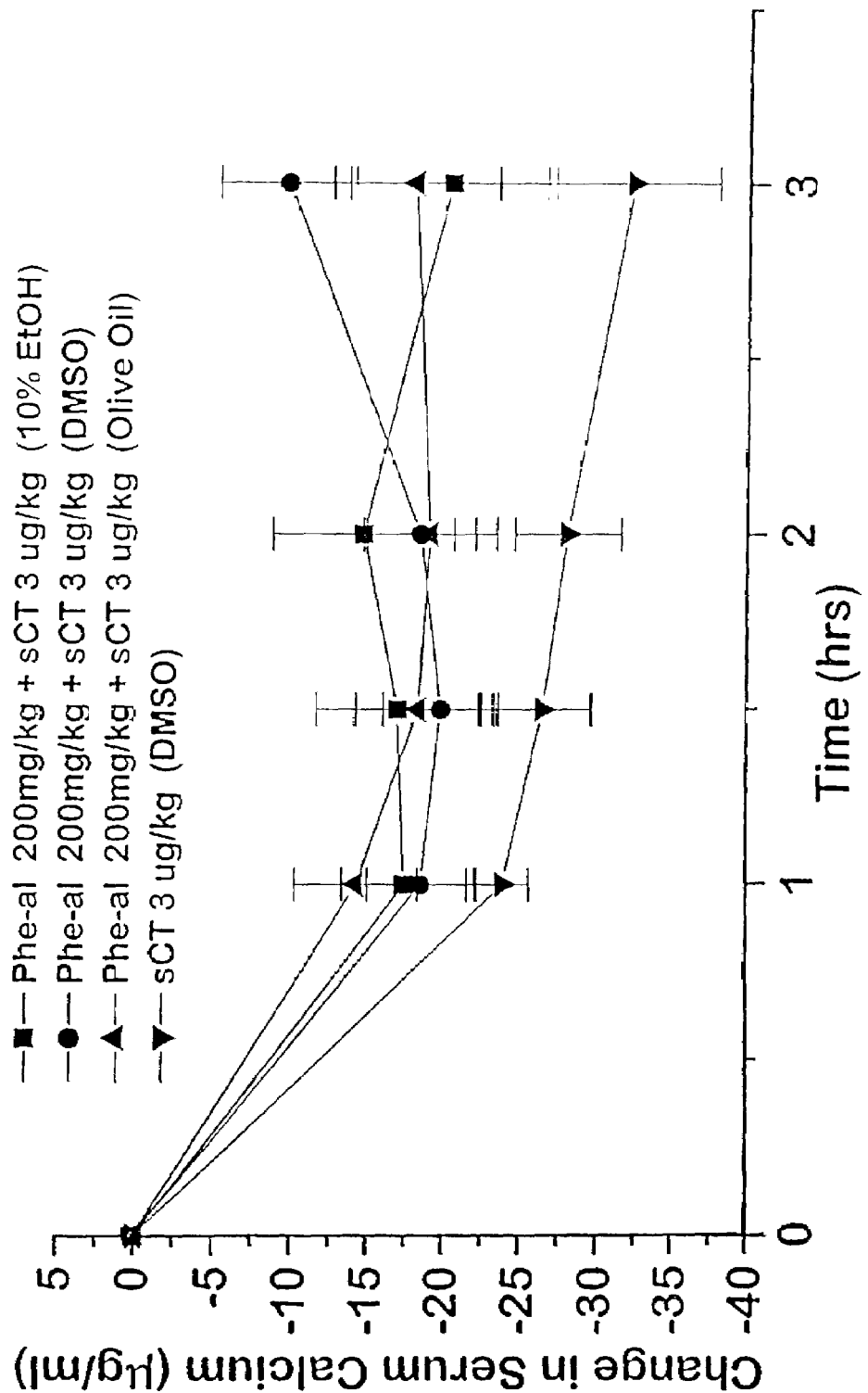
FIG. 7 is a graphic illustration of the results of intraduodenal injection testing in rats using salmon calcitonin with acetylphenylalanine aldehyde carrier in aqueous ethanol, dimethyl sulfoxide (DMSO), and olive oil dosing vehicles, and in a DMSO dosing vehicle alone.

Three samples having 200 mg/kg of acetyl-Phe aldehyde and 3 µg/kg of calcitonin, in aqueous ethanol, dimethyl sulfoxide (DMSO), and olive oil, respectively, were prepared. Additionally a sample of 3 µg/kg of calcitonin in DMSO alone was prepared. The samples were given to rats by intraduodenal injection. The results of the test are illustrated in FIG. 7.

Example 23

Figure 8:
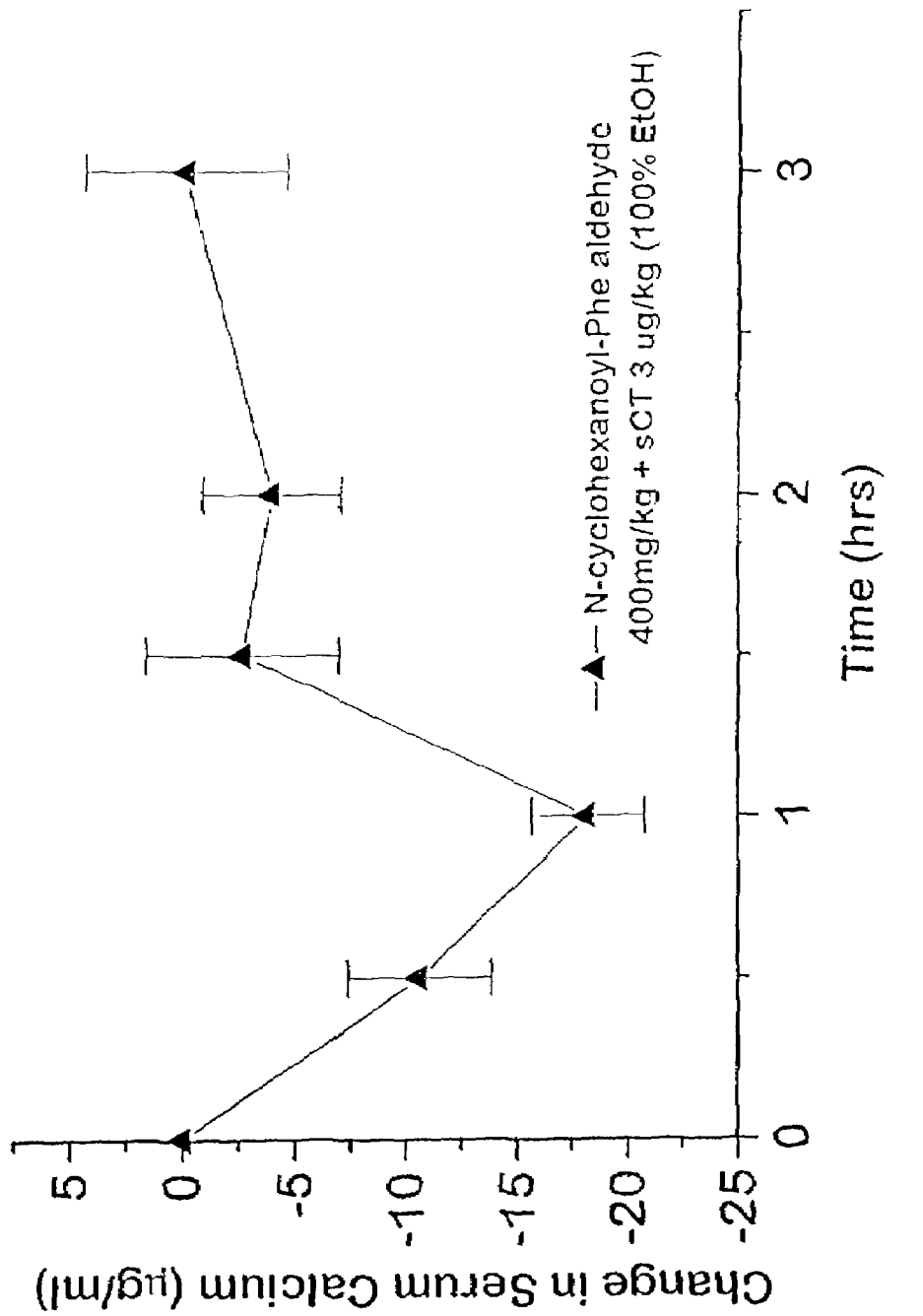
FIG. 8 is a graphic illustration of the results of oral gavage testing in rats using salmon calcitonin with cyclohexanoyl-phenylalanine aldehyde carrier.

A sample having 400 mg/kg of cyclohexanoyl-Phe aldehyde and 3 µg/kg of calcitonin in aqueous ethanol was prepared. The sample was given to fasted rats as described in Example 16. The results of the test are illustrated in FIG. 8.

Example 24

In vivo evaluation of modified amino acid microspheres containing encapsulated calcitonin and soluble modified amino acid carrier/calcitonin system, prepared as described in Example 16, were evaluated in rats. Rats were gavaged with the oral dosing preparations and blood samples were withdrawn at various time intervals for serum calcium concentration determinations.

Nine rats are divided into three groups as follows:
1. calcitonin microspheres: 10 ug calcitonin/kg body weight by oral gavage (3 rats);
2. calcitonin microspheres: 30 ug calcitonin/kg body weight by oral gavage (3 rats); and
3. soluble modified amino acid/calcitonin system: 30 ug calcitonin/kg body weight by oral gavage (3 rats). The rats were pre-dosed with 0.7 meq of aqueous sodium bicarbonate solution prior to administration of the soluble system.

Oral gavage dosing of rats is performed. Calcitonin microspheres are prepared immediately prior to dosing and Group 1 rats and Group 2 rats each receive an appropriate dosage of the microsphere suspension. Group 3 rats receives the unencapsulated calcitonin/modified amino acid system. Approximately 0.5 ml of blood is withdrawn from each rat just prior to dosing ("0" time) and 1 h, 2 h and 3 h post-dosing. Serum from the blood samples are stored at −20° C.

Figure 9:
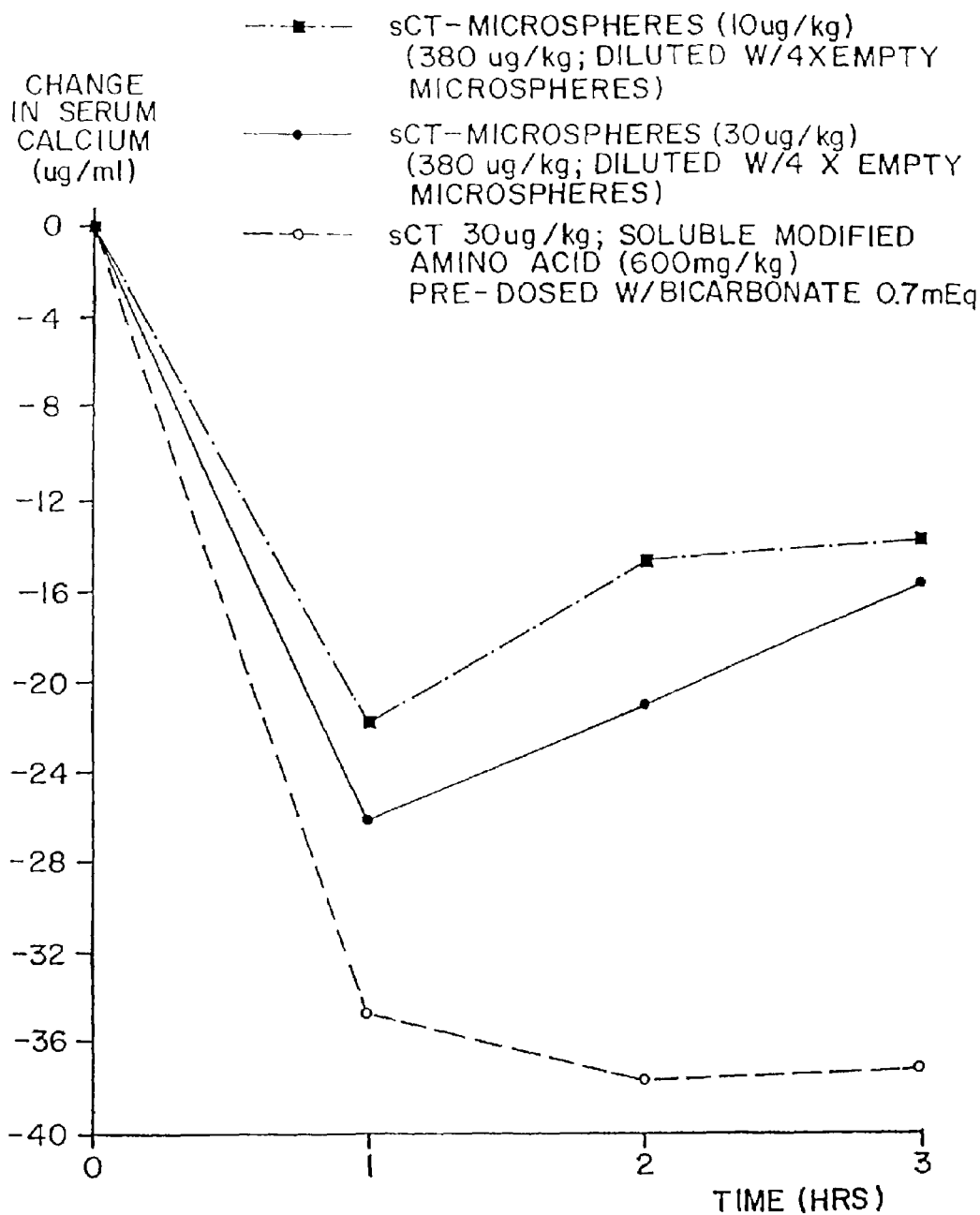
FIG. 9 is a graphic illustration of rat serum calcium levels after oral administration of two dosage levels of a modified amino acid microsphere preparation containing salmon calcitonin and a soluble modified amino acid preparation containing salmon calcitonin after pre-dosing with a sodium bicarbonate solution.

The calcium levels of thawed serum taken from group 1–3 rats are analyzed by conventional methods. Experimental results in rats have demonstrated a significant increase in pharmacological activity (i.e., decreasing serum calcium levels) when calcitonin is orally administered either as a encapsulate in modified amino acid microspheres or a mixture with modified amino acids as compared to basal levels. As shown in FIG. 9, soluble modified amino acid solution containing salmon calcitonin demonstrated a significant increase in pharmacological activity (i.e., decreasing serum calcium levels) when compared to basal levels after oral administration.

Example 25

Figure 10:
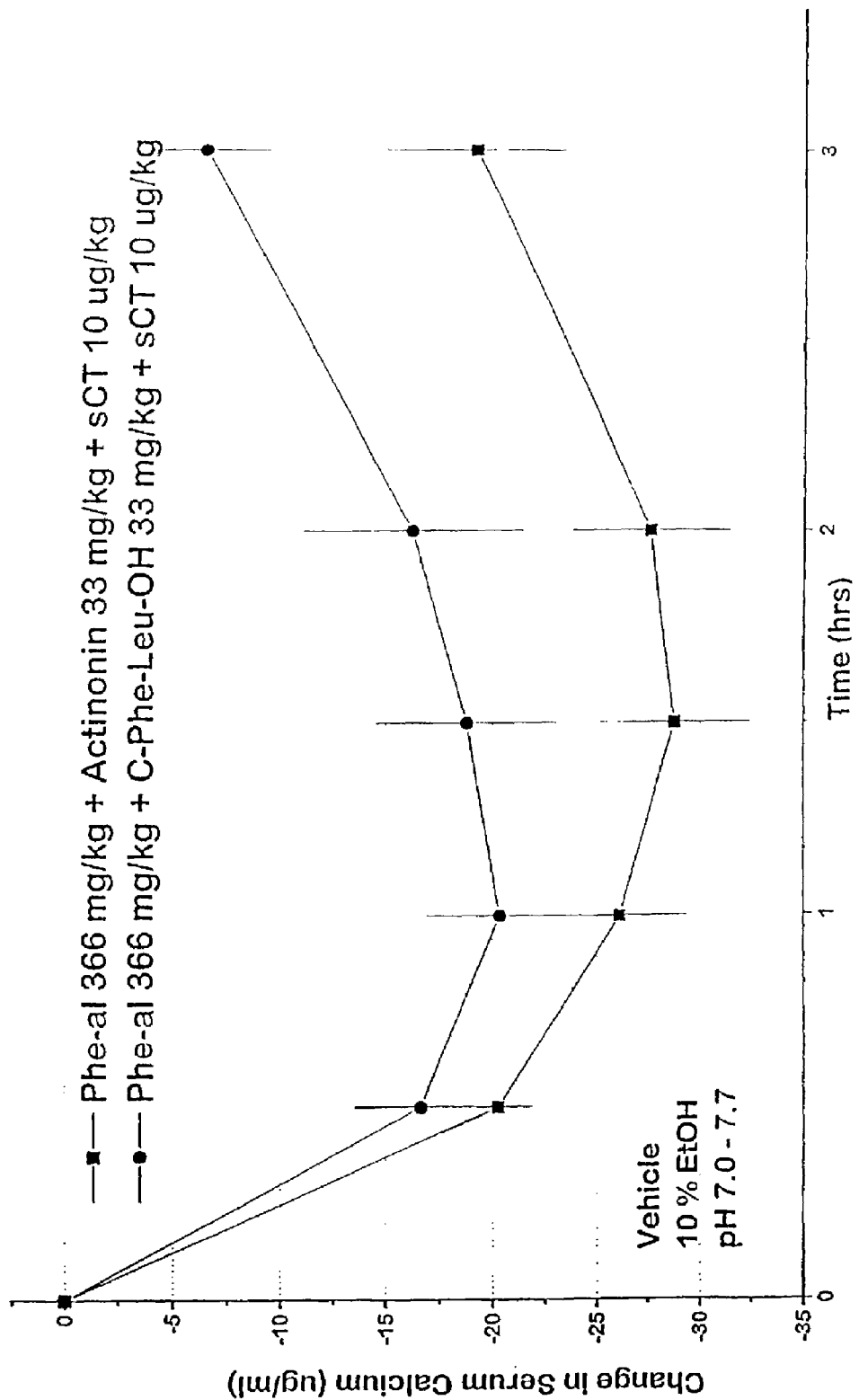
FIG. 10 is a graphic illustration of the results of oral gavage testing in rats using salmon calcitonin with acetyl-Phe aldehyde, actinonin, and carbomethoxy-Phe-Leu-OH carriers.

Two samples having 366 mg/kg of acetyl-Phe aldehyde, 33 mg/kg of actinonin and 10 µg/kg of calcitonin, 366 mg of acetyl Phe aldehyde, 33 mg/kg of carbomethoxy-Phe-Leu-OH and 10 µg/kg of calcitonin, respectively, were prepared. The samples were given to fasted rats as described in Example 14. The results of the test are illustrated in FIG. 10.

Example 26

Figure 11:
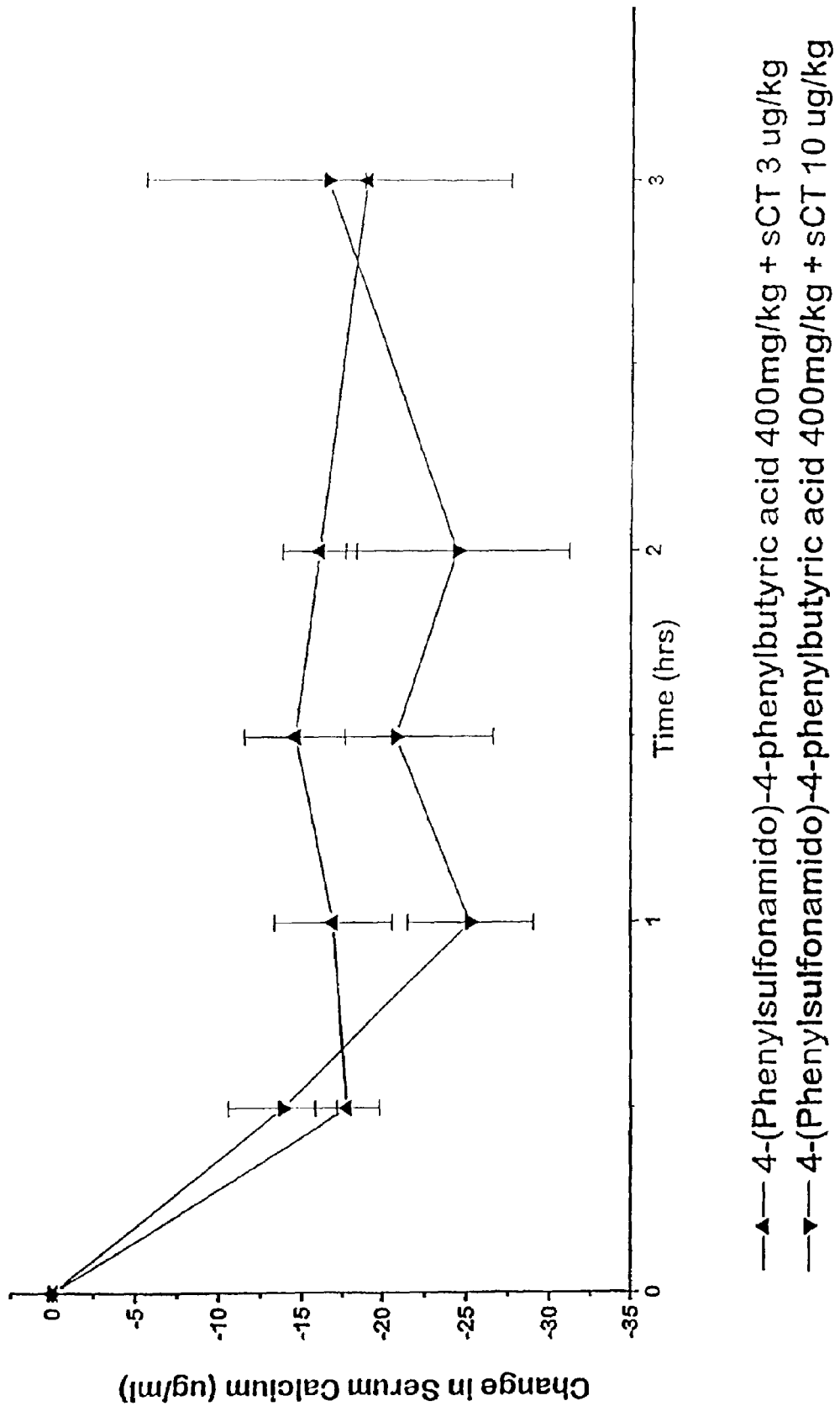
FIG. 11 is a graphic illustration of the results of oral gavage testing in rats using salmon calcitonin with 4-(phenylsulfonamido)-4-phenylbutyric acid carrier.

Two samples having 400 mg/kg of 4-(phenylsulfonamido)-4-phenylbutyric acid and 3 µg/kg of calcitonin, 400 mg/kg of 4-(phenylsulfonamido)-4-phenylbutyric acid and 10 µg/kg of calcitonin, respectively were prepared. The samples were given to fasted rats as described in Example 14. The results of the test are illustrated in FIG. 11.

Example 27

Figure 12:
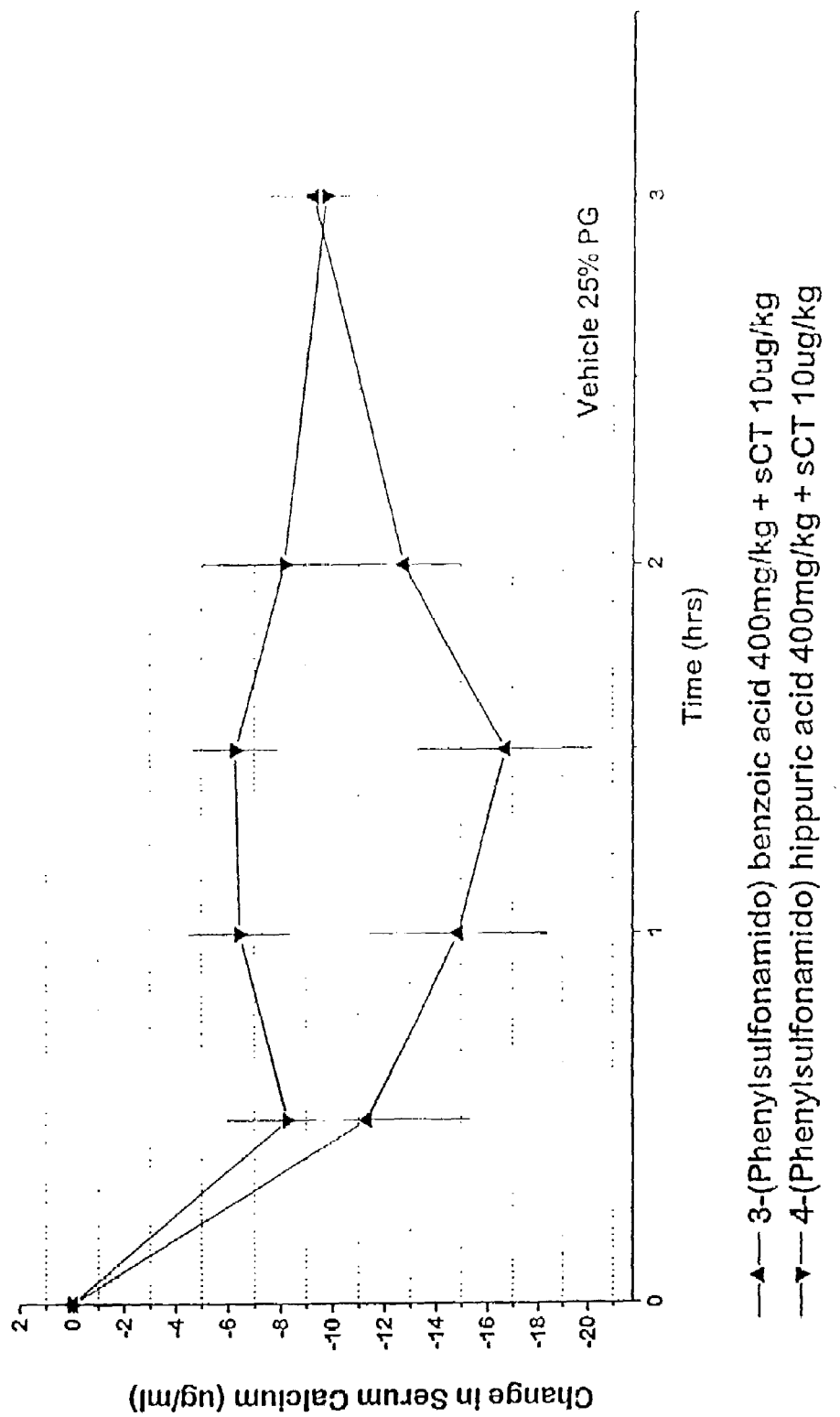
FIG. 12 is a graphic illustration of the results of oral gavage testing in rats using salmon calcitonin with 3-(phenylsulfonamido)benzoic acid and 4-(phenylsulfonamido)-hippuric acid carriers.

Two samples having 400 mg/kg of 3-(phenylsulfonamido)benzoic acid and 10 µg/kg of calcitonin, 400 mg/kg of 4-(phenylsulfonamido)hippuric acid and 10 µg/kg of calcitonin, respectively were prepared. The samples were given to fasted rats as described in Example 14. The results of the test are illustrated in FIG. 12.

Example 28

Figure 13:
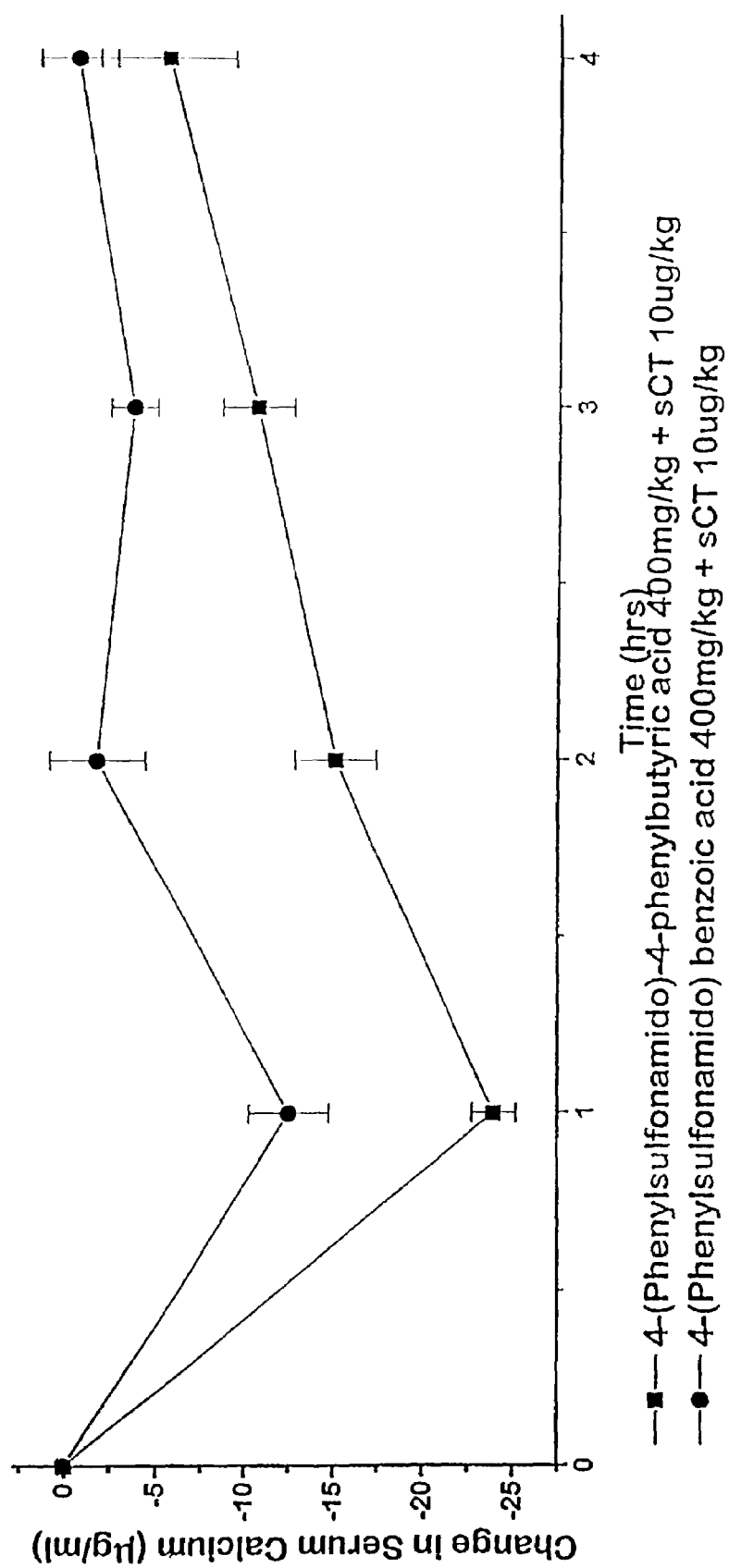
FIG. 13 is a graphic illustration of the results of oral gavage testing in rats using salmon calcitonin with 4-(phenylsulfonamido)-4-phenylbutyric acid and 4-(phenylsulfonamido)benzoic acid carriers.

Two samples having 400 mg/kg of 4-(phenylsulfonamido)-4-phenylbutyric acid and 10 µg/kg of calcitonin, 400 mg/kg of 4-(phenylsulfonamido)benzoic acid and 10 µg/kg of calcitonin, respectively were prepared. The samples were given to fasted rats as described in Example 14. The results of the test are illustrated in FIG. 13.

Example 29

Figure 14:
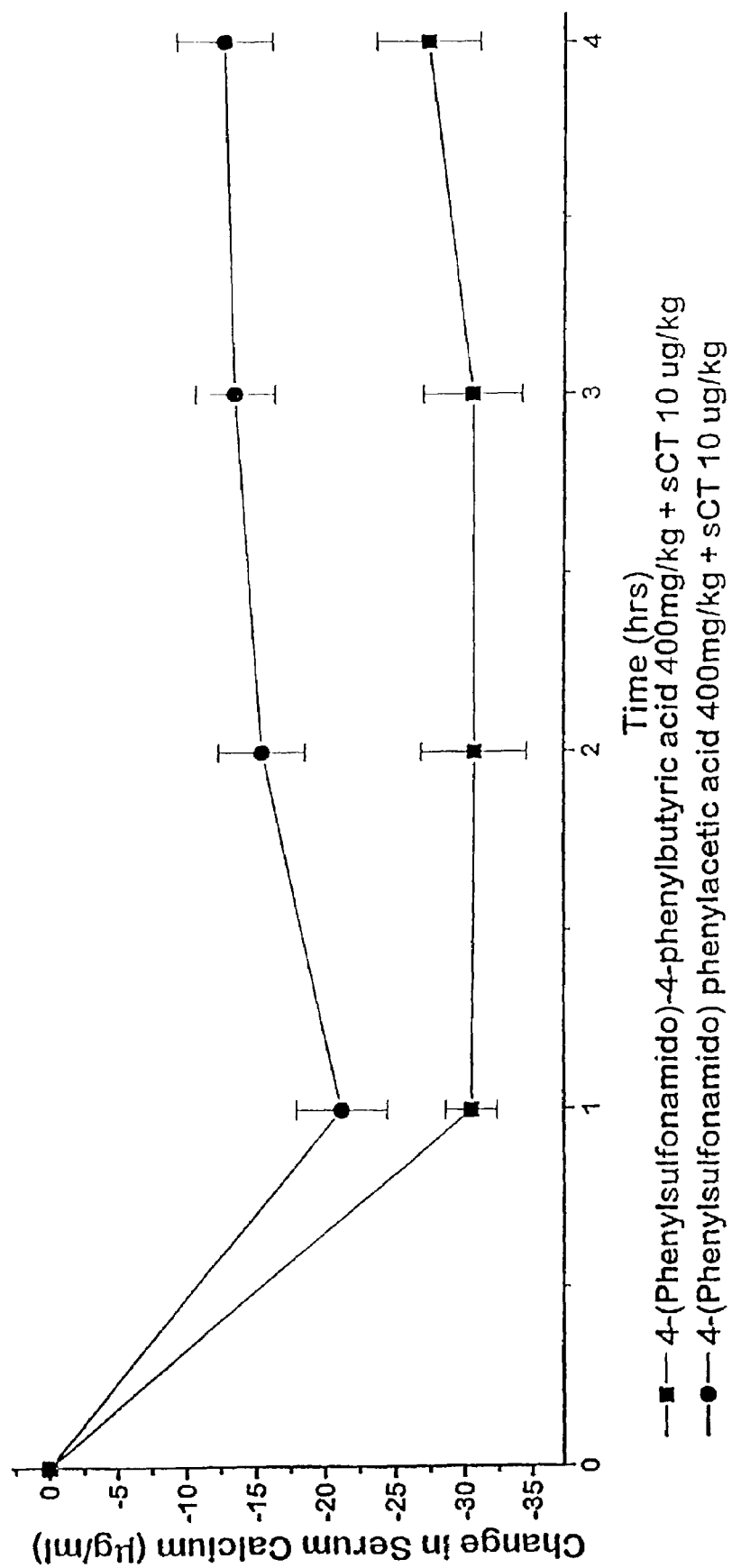
FIG. 14 is a graphic illustration of the results of oral gavage testing in rats using salmon calcitonin with 4-(phenylsulfonamido)-4-phenylbutyric acid and 4-(phenylsulfonamido)phenylacetic acid carriers.

Two samples having 400 mg/kg of 4-(phenylsulfonamido)-4-phenylbutyric acid and 10 µg/kg of calcitonin, 400 mg/kg of 4-(phenylsulfonamido)phenylacetic acid and 10 µg/kg of calcitonin, respectively were prepared. The samples were given to fasted rats as described in Example 14. The results of the test are illustrated in FIG. 14.

In Vivo Evaluation of Interferon Preparations in Rats

Following the procedure described herein samples containing the carriers of the subject invention, in a Trizma® hydrochloride buffer solution (Tris-HCl) at a pH of about 7–8, and interferon α2b were prepared. The animals were administered the drug by oral gavage. The delivery was evaluated by using an ELISA assay for human interferon α.

Example 30

Figure 15:
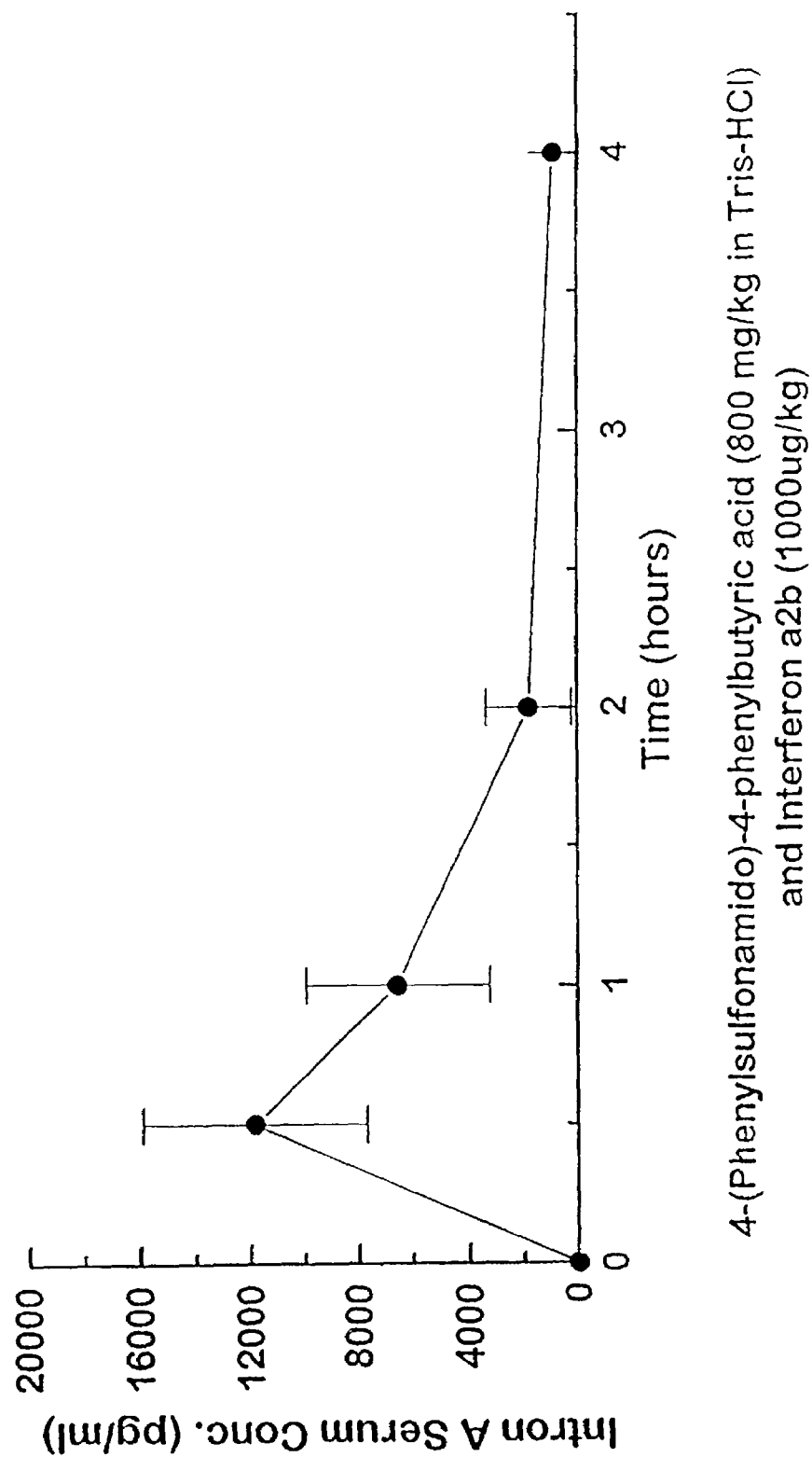
FIG. 15 is a graphic illustration of the results of oral gavage testing in rats using interferon α2b (rhIFN) with 4-(phenylsulfonamido)-4-phenylbutyric acid carrier.

A sample having 800 mg/kg of 4-(phenylsulfona-mido)-4-phenylbutyric acid in a buffered solution and 1000 μg/kg of interferon α2b was prepared. The sample was given to fasted rats as described in Example 14. The results of the test are illustrated in FIG. 15.

Example 31

Figure 16:
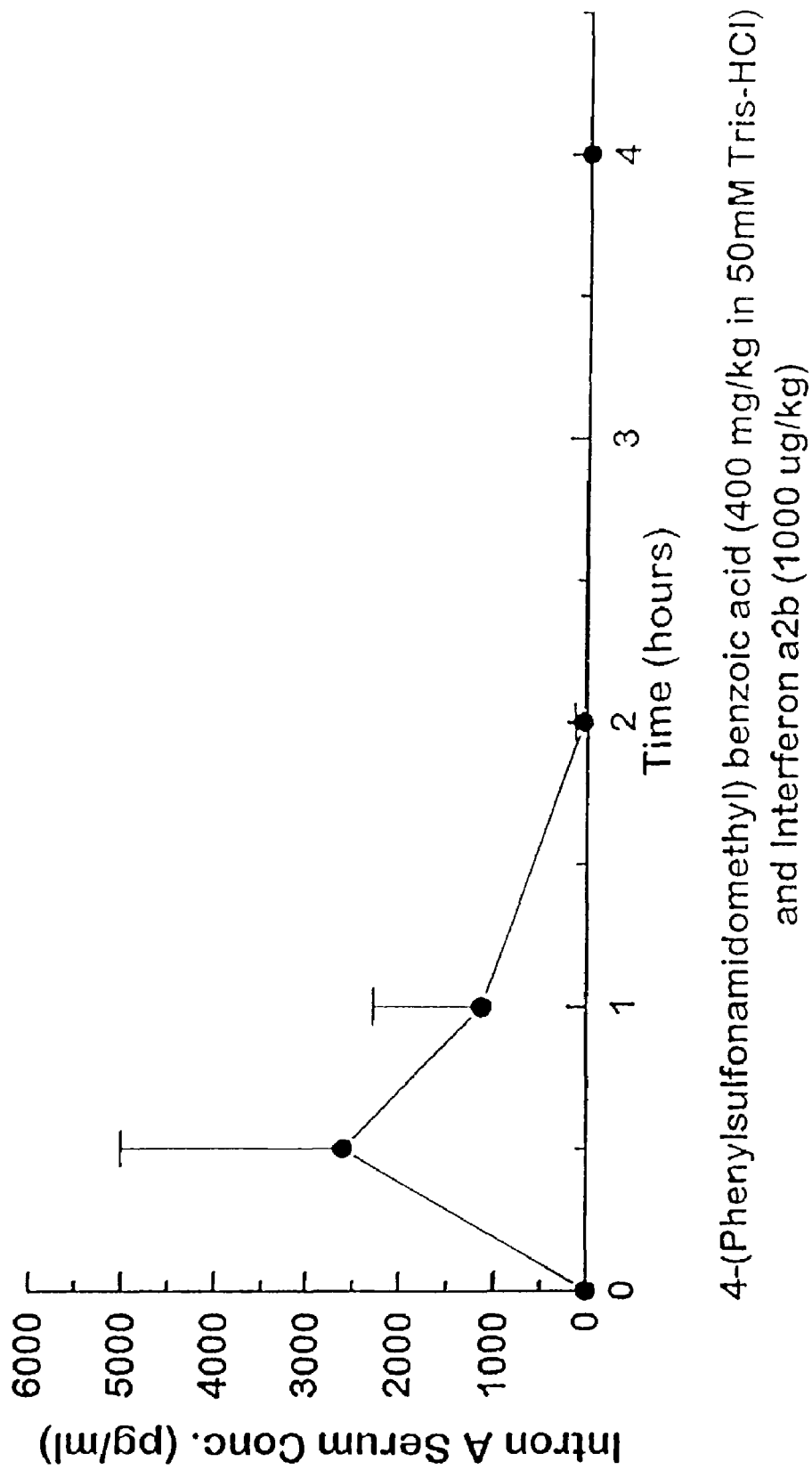
FIG. 16 is a graphic illustration of the results of oral gavage testing in rats using interferon α2b with 4-(phenylsulfonamidomethyl)benzoic acid carrier.

A sample having 400 mg/kg of 4-(phenylsulfonamido-methyl)benzoic acid in a buffered solution and 1000 μg/kg of interferon α2b was prepared. The sample was given to fasted rats as described in Example 14. The results of the test are illustrated in FIG. 16.

Example 32

Figure 17:
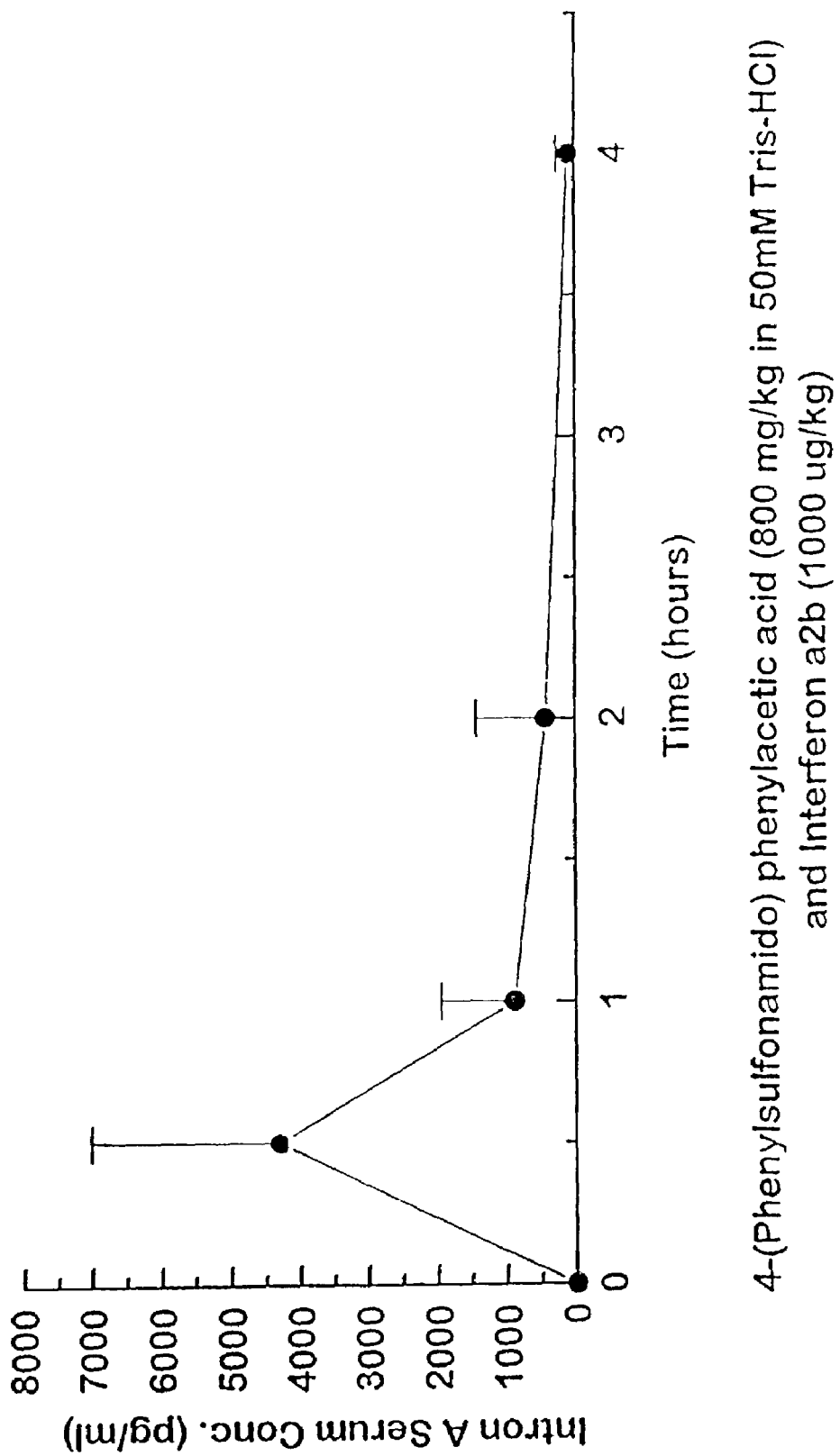
FIG. 17 is a graphic illustration of the results of oral gavage testing in rats using interferon α2b with 4-(phenylsulfonamido)phenylacetic acid as carrier.

A sample having 800 mg/kg of 4-(phenylsulfona-mido) phenylacetic acid in a buffered solution and 1000 μg/kg of interferon α2b was prepared. The sample was given to fasted rats as described in Example 14. The results of the test are illustrated in FIG. 17.

Example 33

Figure 18:
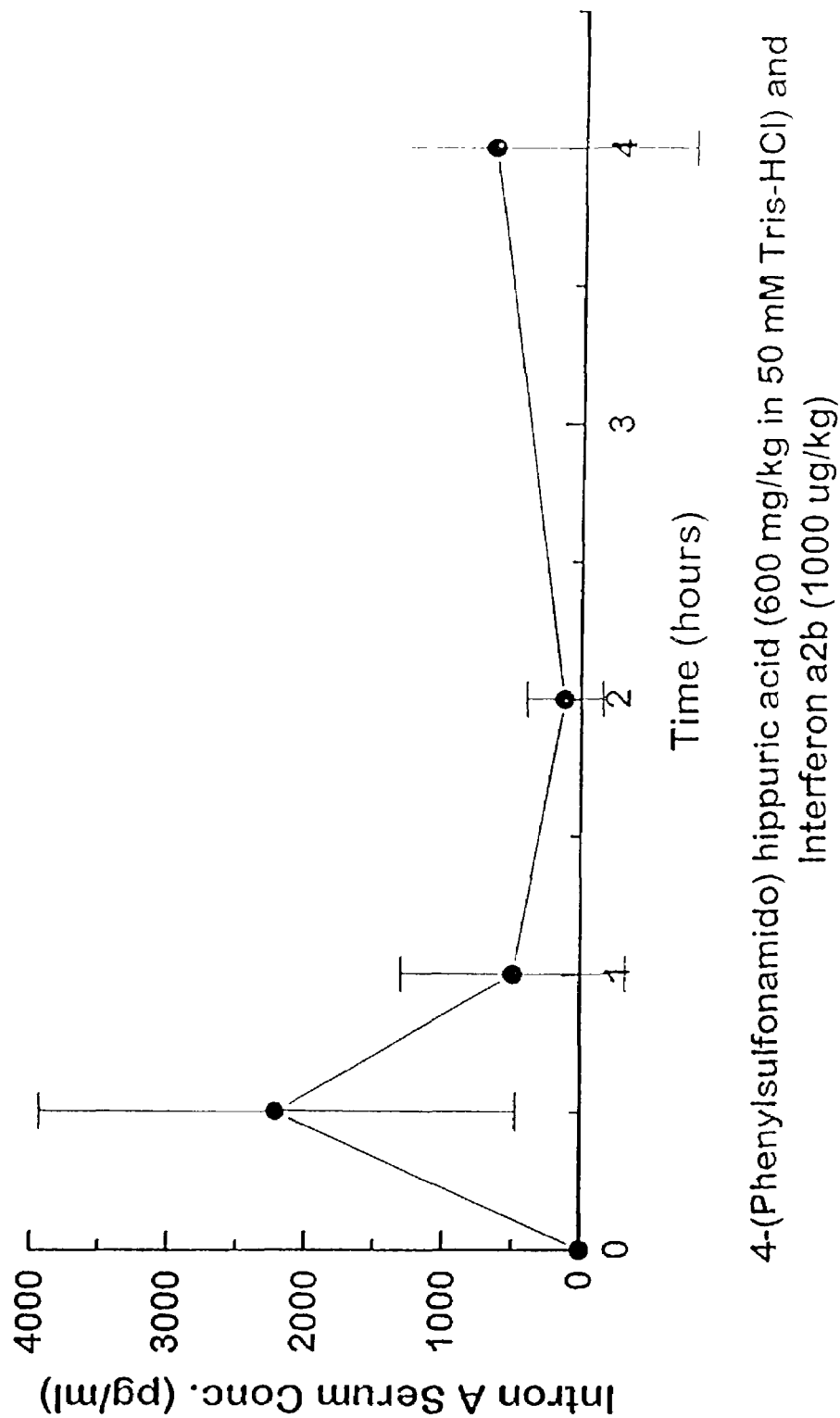
FIG. 18 is a graphic illustration of the results of oral gavage testing in rats using interferon α2b with 4-(phenylsulfonamido)hippuric acid carrier.

A sample having 600 mg/kg of 4-(phenylsulfona-mido) hippuric acid in a buffered solution and 1000 μg/kg of interferon α2b was prepared. The sample was given to fasted rats as described in Example 14. The results of the test are illustrated in FIG. 18.

In Vivo Evaluation of Growth Hormone Preparations in Rats

Following the procedure described herein samples containing the carriers of the subject invention and growth hormone were prepared. The animals were administered the drug by oral gavage. The delivery was evaluated by using an ELISA assay for growth hormone.

Example 34

Figure 19:
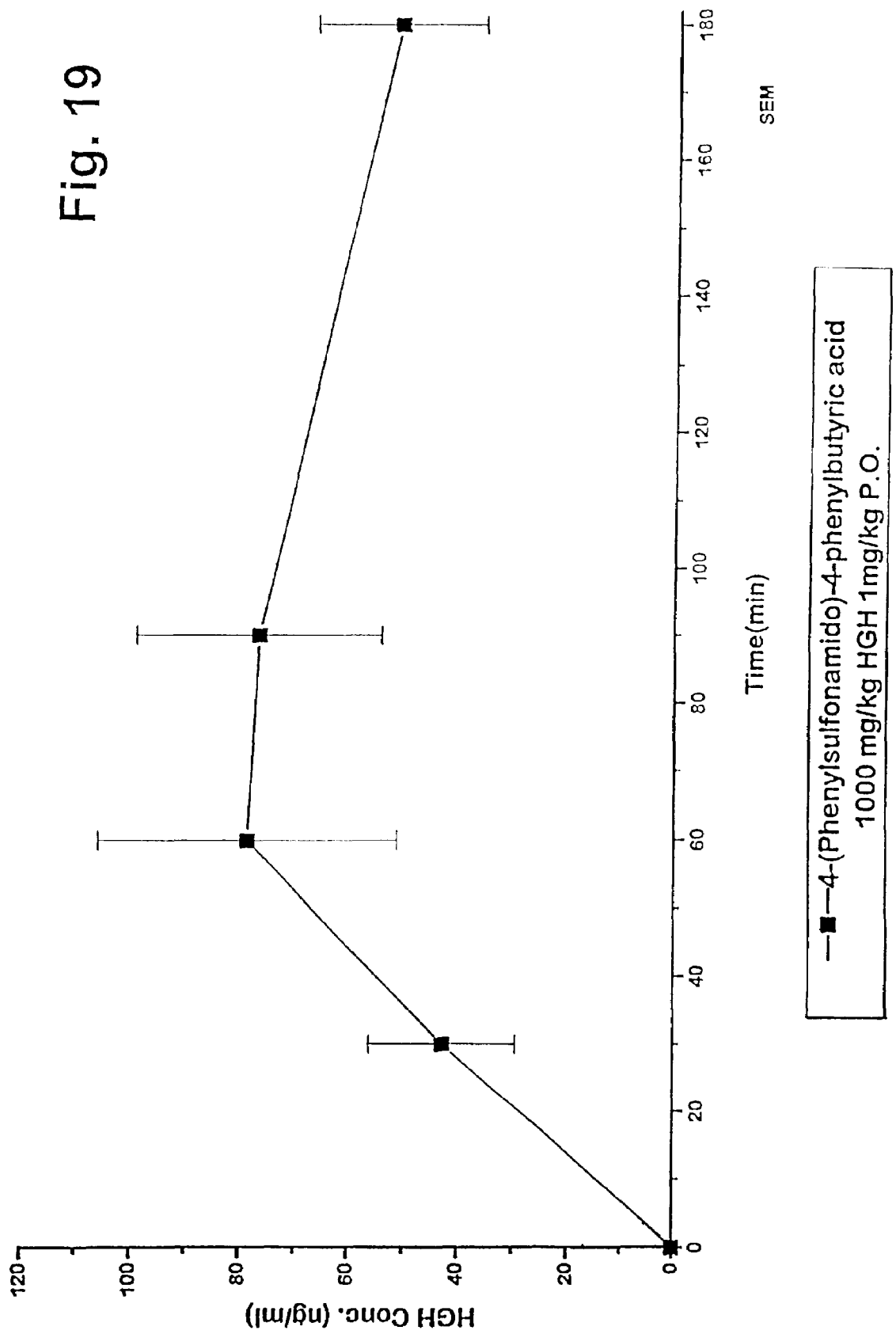
FIGS. 19 and 20 are graphic illustrations of the results of oral gavage testing in hypophysectomized rats using growth hormone alone and at two dosage levels with 4-(phenylsulfonamido)-4-phenylbutyric acid carrier.

A sample having 1000 mg/kg of 4-(phenylsulfona-mido)-4-phenylbutyric acid and 1 mg/kg of growth hormone was prepared. The sample was given to hypophysectomized rats as described in Example 14. The results of the test are illustrated in FIG. 19.

Example 35

Figure 20:
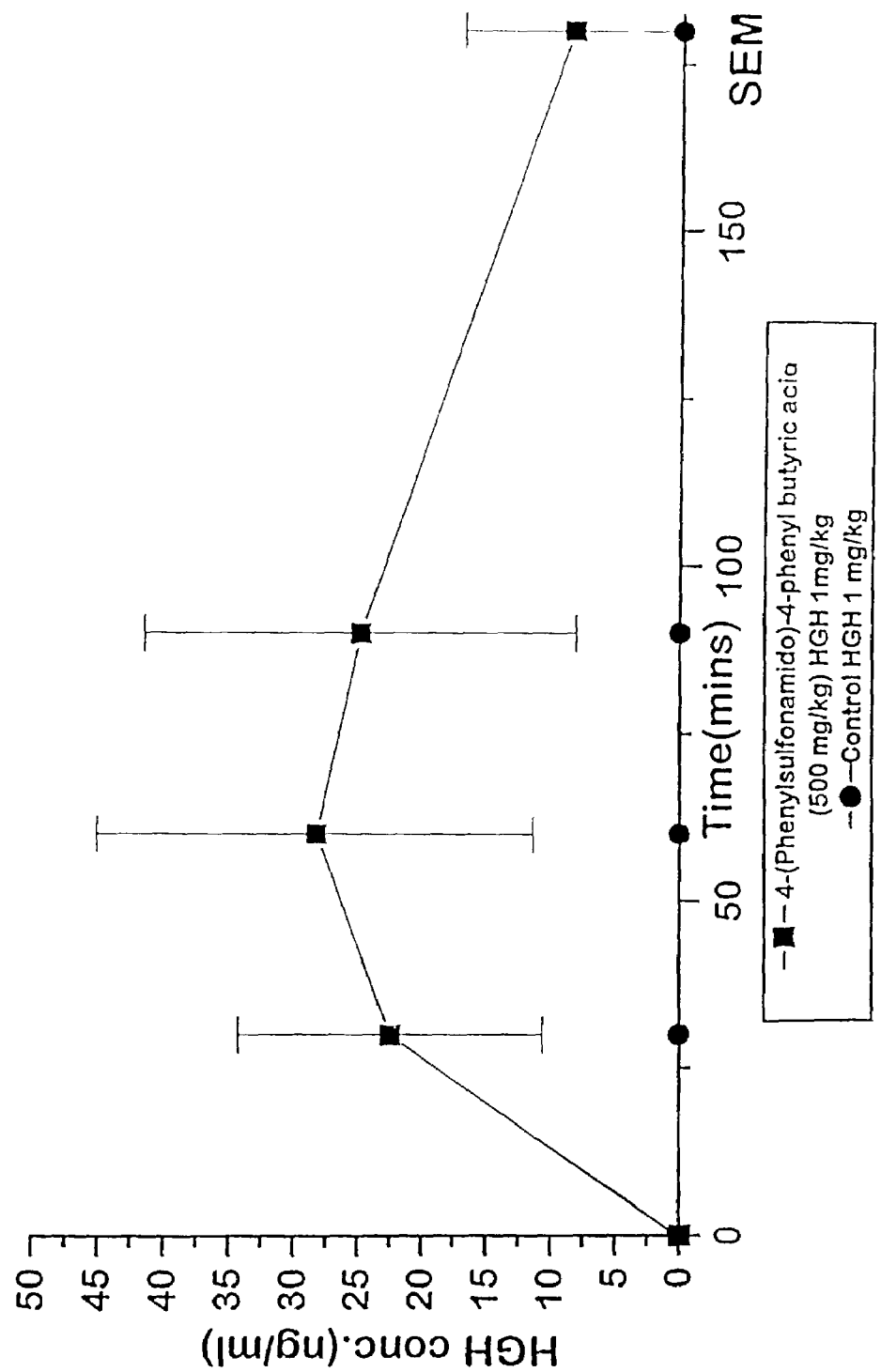

A sample having 500 mg/kg of 4-(phenylsulfona-mido)-4-phenylbutyric acid and 1 mg/kg of growth hormone was prepared. In a comparison a group of hypophysectomized rats were given samples of growth hormone without a carrier. The samples were given to hypophysectomized rats as described in Example 14. The results of the test are illustrated in FIG. 20.

Example 36

Figure 21:
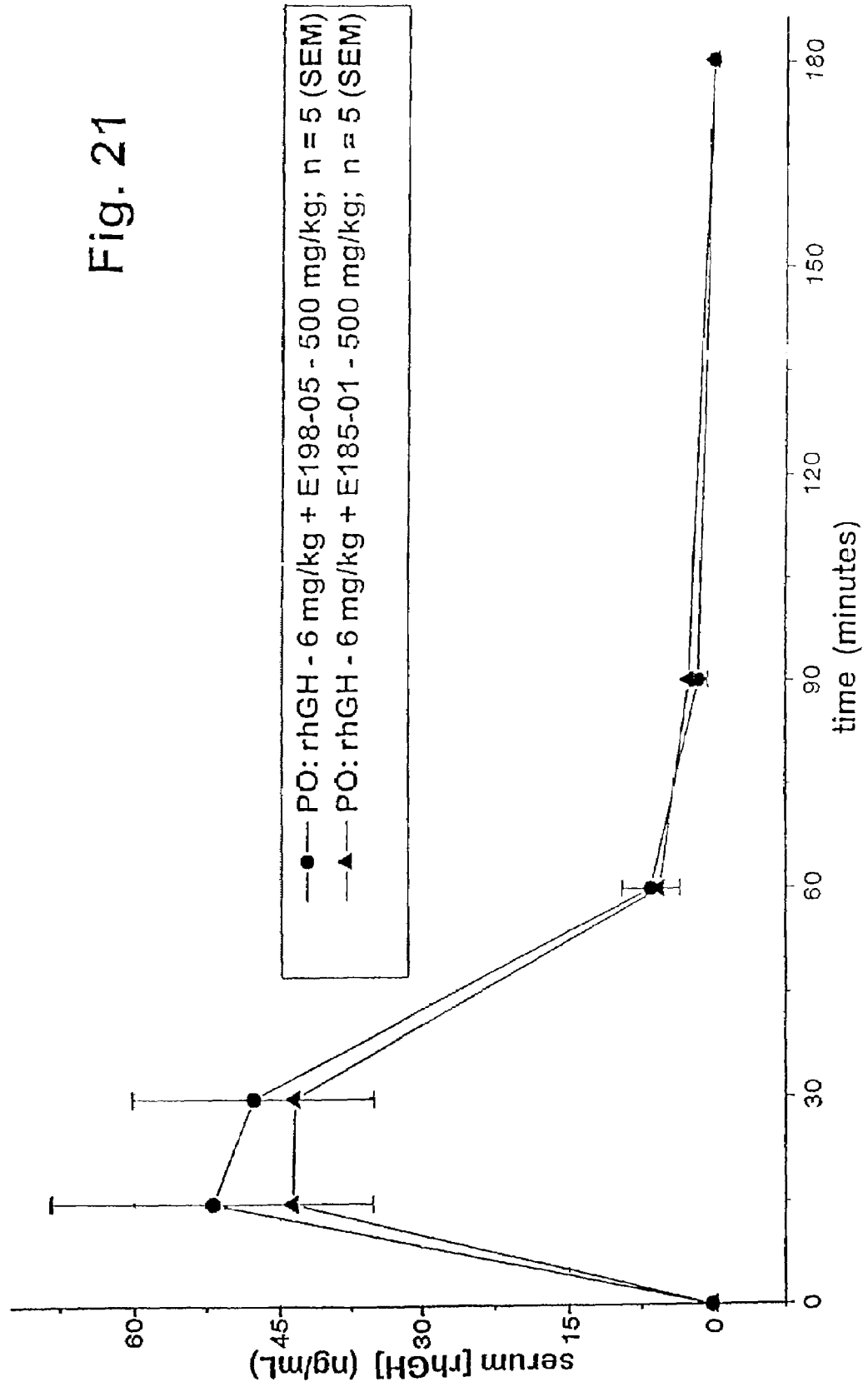
FIG. 21 is a graphic illustration of the results of oral gavage testing in normal rats using growth hormone with 4-(phenylsulfonamido)-4-phenylbutyric acid carrier.

Two samples having 500 mg/kg of 4-(phenylsulfona-mido)-4-phenylbutyric acid and 6 mg/kg of growth hormone were prepared. The samples were given to normal rats as described in Example 14. The results of the tests are illustrated in FIG. 21.

In Vivo Evaluation of Cromoglycolate Preparations in Rats

Example 37

Figure 22:
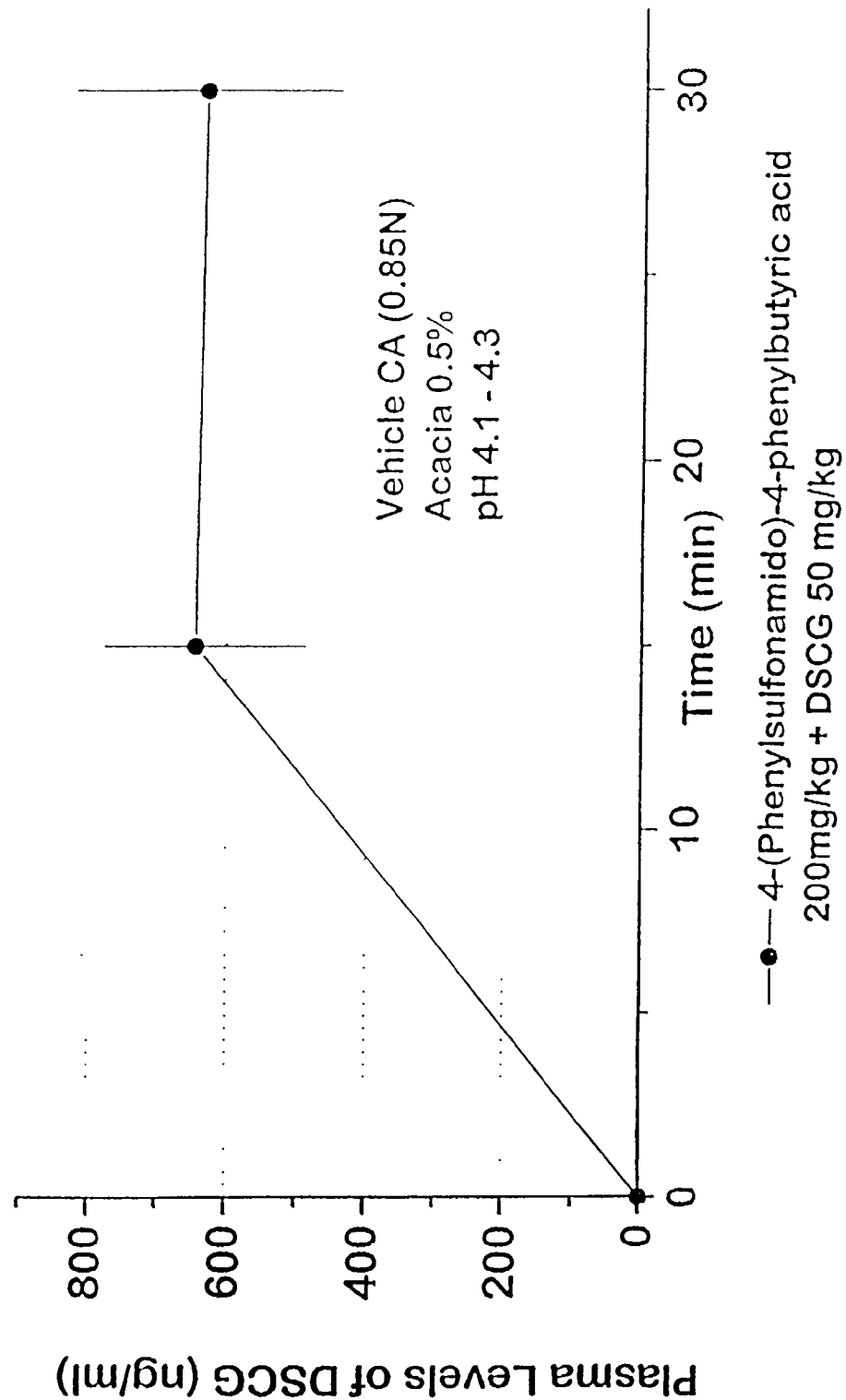
FIG. 22 is a graphic illustration of the results of oral gavage testing in rats using disodium cromoglycate with 4-(phenylsulfonamido)-4-phenylbutyric acid as carrier.

Following the procedure described herein samples containing the carriers of the subject invention and disodium cromoglycolate were prepared. The sample, in 0.85N citric acid and 0.5% acacia, contained 200 mg/kg of 4-(phenyl-sulfonamido)-4-phenylbutyric acid and 50 mg/kg of disodium cromoglycate. The animals were administered the drug by oral gavage. The delivery was evaluated by using the procedure described by A. Yoshimi in *Pharmcobio-Dyn.*, 15, pages 681–686, (1992). The results of the tests are illustrated in FIG. 22.

As clearly illustrated by the data in the Examples and Figures the use of compositions of the subject invention show significant advantages for the delivery of biologically active agents.

All patents, applications, and publications mentioned herein are incorporated by reference herein.

Many variations of the present invention will suggest themselves to those skilled in the art in light of the above detailed disclosure. For example, poly (amino acids) which are formed by a bond other than an amide bond, e.g., an ester or an anhydride linkage, may be derivatized and modified for use as carriers in accordance with the present invention. All such modifications are within the full intended scope of the appended claims.

What is claimed is:

1. A composition comprising:
   (A) at least one biologically-active agent; and
   (B) a compound having the formula:

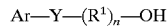

wherein:

Ar is a substituted or unsubstituted phenyl;

Y is

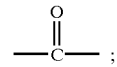

$R^1$ has the formula

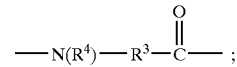

wherein:

$R^3$ is $C_1$ to $C_{24}$ alkyl;

$R^4$ is hydrogen, $C_1$ to $C_4$ alkyl, or $C_1$ to $C_4$ alkenyl; and n is equal to 1.

2. The composition of claim 1, wherein said biologically-active agent is selected from the group consisting of a peptide, a polysaccharide, a mucopolysaccharide, a carbohydrate, a lipid or any combination thereof.

3. The composition of claim 2, wherein said biologically-active agent is a peptide.

4. The composition of claim 2, wherein said biologically-active agent is a polysaccharide.

5. The composition of claim 2, wherein said biologically-active agent is a mucopolysaccharide.

6. The composition of claim 1, wherein said biologically-active agent is selected from the group consisting of human growth hormone, bovine growth hormone, growth hormone-releasing hormone, an interferon, interleukin-I, interleukin-II, insulin, heparin, low molecular weight heparin, calcitonin, erythropoietin, atrial naturetic factor, an antigen, a monoclonal antibody, somatostatin, adrenocorticotropin, gonadotropin releasing hormone, oxytocin, vasopressin, cromolyn sodium, vancomycin, desferrioxamine, or any combination thereof.

7. The composition of claim 6, wherein said biologically-active agent is human growth hormone.

8. The composition of claim 6, wherein said biologically-active agent is interferon.

9. The composition of claim 6, wherein said biologically-active agent is insulin.

10. The composition of claim 6, wherein said biologically-active agent is heparin.

11. The composition of claim 6, wherein said biologically-active agent is low molecular weight heparin.

12. The composition of claim 6, wherein said biologically-active agent is calcitonin.

13. The composition of claim 6, wherein said biologically-active agent is erythropoietin.

14. The composition of claim 6, wherein said biologically-active agent is an antigen.

15. The composition of claim 6, wherein said biologically-active agent is cromolyn sodium.

16. A dosage unit form comprising
(A) the composition of claim 1; and
(B) (a) an excipient
  (b) a diluent,
  (c) a disintegrant,
  (d) a lubricant,
  (e) a plasticizer,
  (f) a colorant,
  (g) a dosing vehicle, or
  (h) any combination thereof.

17. The dosage unit form of claim 16, comprising a tablet, a capsule, or a liquid.

18. The dosage unit form of claim 17, wherein said biologically-active agent is selected from the group consisting of a peptide, a polysaccharide, a mucopolysaccharide, a carbohydrate, a lipid or any combination thereof.

19. The dosage unit form of claim 18, wherein said biologically-active agent is a peptide.

20. The dosage unit form of claim 18, wherein said biologically-active agent is a polysaccharide.

21. The dosage unit form of claim 18, wherein said biologically-active agent is a mucopolysaccharide.

22. The dosage unit form of claim 17, wherein said biologically-active agent is selected from the group consisting of human growth hormone, bovine growth hormone, growth hormone-releasing hormone, an interferon, interleukin-I, interleukin-II, insulin, heparin, low molecular weight heparin, calcitonin, erythropoietin, atrial naturetic factor, an antigen, a monoclonal antibody, somatostatin, adrenocorticotropin, gonadotropin releasing hormone, oxytocin, vasopressin, cromolyn sodium, vancomycin, desferrioxamine, or any combination thereof.

23. The dosage unit form of claim 22, wherein said biologically-active agent is human growth hormone.

24. The dosage unit form of claim 22, wherein said biologically-active agent is interferon.

25. The dosage unit form of claim 22, wherein said biologically-active agent is insulin.

26. The dosage unit form of claim 22, wherein said biologically-active agent is heparin.

27. The dosage unit form of claim 22, wherein said biologically-active agent is low molecular weight heparin.

28. The dosage unit form of claim 22, wherein said biologically-active agent is calcitonin.

29. The dosage unit form of claim 22, wherein said biologically-active agent is erythropoietin.

30. The dosage unit form of claim 22, wherein said biologically-active agent is an antigen.

31. The dosage unit form of claim 22, wherein said biologically-active agent is cromolyn sodium.

32. A method for preparing a composition, said method comprising mixing:
(A) at least one biologically-active agent; and
(B) a compound having the formula:

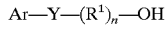

wherein:
Ar is a substituted or unsubstituted phenyl;
Y is

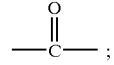

$R^1$ has the formula

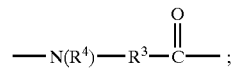

wherein:
$R^3$ is $C_1$ to $C_{24}$ alkyl, ($C_1$ to $C_{10}$ alkyl) phenyl, or phenyl ($C_1$ to $C_{10}$ alkyl);
$R^4$ is hydrogen, $C_1$ to $C_4$ alkyl, or $C_1$ to $C_4$ alkenyl; and
n is equal to 1.

33. The method of claim 32, wherein said biologically-active agent is selected from the group consisting of a peptide, a polysaccharide, a mucopolysaccharide, a carbohydrate, a lipid or any combination thereof.

34. The method of claim 33, wherein said biologically-active agent is a peptide.

35. The method of claim 33, wherein said biologically-active agent is a polysaccharide.

36. The method of claim 33, wherein said biologically-active agent is a mucopolysaccharide.

37. The method of claim 32, wherein said biologically-active agent is selected from the group consisting of human growth hormone, bovine growth hormone, growth hormone-releasing hormone, an interferon, interleukin-I, interleukin-II, insulin, heparin, low molecular weight heparin, calcitonin, erythropoietin, atrial naturetic factor, an antigen, a monoclonal antibody, somatostatin, adrenocorticotropin, gonadotropin releasing hormone, oxytocin, vasopressin, cromolyn sodium, vancomycin, desferrioxamine, or any combination thereof.

38. The method of claim 37, wherein said biologically-active agent is human growth hormone.

39. The method of claim 37, wherein said biologically-active agent is interferon.

40. The method of claim 37, wherein said biologically-active agent is insulin.

41. The method of claim 37, wherein said biologically-active agent is heparin.

42. The method of claim 37, wherein said biologically-active agent is low molecular weight heparin.

43. The method of claim 37, wherein said biologically-active agent is calcitonin.

44. The method of claim 37, wherein said biologically-active agent is erythropoietin.

45. The method of claim 37, wherein said biologically-active agent is an antigen.

46. The method of claim 37, wherein said biologically-active agent is cromolyn sodium.

* * * * *